United States Patent [19]
Beach et al.

[11] Patent Number: 5,919,997
[45] Date of Patent: Jul. 6, 1999

[54] TRANSGENIC MICE HAVING MODIFIED CELL-CYCLE REGULATION

[75] Inventors: David H. Beach, Huntington Bay; Manuel Serrano, Mill Neck; Ronald A. DePinho, Pelham Manor, all of N.Y.

[73] Assignees: Cold Spring Habor Labortary, Cold Spring Habor, N.Y.; Albert Einstein College of Medicine of Yeshiva University, Bronx, N.Y.

[21] Appl. No.: 08/627,610

[22] Filed: Apr. 4, 1996

Related U.S. Application Data

[63] Continuation-in-part of application No. 08/581,918, Jan. 2, 1996, which is a continuation-in-part of application No. 08/497,214, Jun. 30, 1995, which is a continuation-in-part of application No. 08/346,147, Nov. 29, 1994, which is a continuation-in-part of application No. 08/306,511, Sep. 14, 1994, which is a continuation-in-part of application No. 08/248,812, May 25, 1994, which is a continuation-in-part of application No. 08/227,371, Apr. 14, 1994, which is a continuation-in-part of application No. 08/154,915, Nov. 18, 1993.

[51] Int. Cl.$^6$ ............................ C12N 15/00; C12N 15/09; C12N 15/63; C12N 5/00

[52] U.S. Cl. ................. 800/18; 800/25; 800/22; 800/3; 435/455; 435/463; 435/467; 435/325; 435/320.1; 435/91.2; 424/9.21

[58] Field of Search ...................... 800/2, 18, 25, 800/22, 3; 435/325, 320.1, 172.3, 69.1, 69.8, 91.2, 455, 463, 467; 424/93.21, 9.2, 9.21; 536/23.1, 23.5, 24.31; 935/23, 78, 79, 70, 71

[56] References Cited

PUBLICATIONS

Houdebine, Journal of Biotechnology, vol. 34, pp. 269–287, 1994.
Wall, Theriogenology, vol. 45, pp. 57–68, 1996.
Kappel et al., Current Opinion in Biotechnology, vol. 3, pp. 548–553, 1992.
Bradley et al., Biotechnology, vol. 10, pp. 534–539, May 1992.
Stojek & Wagner, Genetic Engineering, vol. 10, pp. 221–246, 1988.
Mansour et al., Nature, vol. 336, pp. 349–352, Nov. 24, 1988.
Serrano et al., Nature, vol. 366, pp. 704–707, Dec. 16, 1993.

*Primary Examiner*—Deborah Crouch
*Assistant Examiner*—Jill D. Martin
*Attorney, Agent, or Firm*—Foley, Hoag & Eliot, LLP; Matthew P. Vincent, Esq.; Anita Varma, Esq.

[57] ABSTRACT

The present invention relates to transgenic mice in which the biological function of at least one cell cycle regulatory proteins of the INK4 family is altered.

11 Claims, 2 Drawing Sheets

5,919,997

TRANSGENIC MICE HAVING MODIFIED CELL-CYCLE REGULATION

RELATED APPLICATIONS

This application is a continuation-in-part of U.S. Ser. No. 08/581,918 filed Jan. 2, 1996 which is a continuation-in-part of U.S. Ser. No. 08/497,214 filed Jun. 30, 1995, which is a continuation-in-part of U.S. Ser. No. 08/346,147 filed Nov. 29, 1994, which is a continuation-in-part of U.S. Ser. No. 08/306,511 filed Sep. 14, 1994, which is a continuation-in-part of U.S. Ser. No. 08/248,812 filed May 25, 1994, which is a continuation-in-part of U.S. Ser. No. 08/227,371 filed Apr. 14, 1994, which is a continuation-in-part of U.S. Ser. No. 08/154,915 filed Nov. 18, 1993. The teachings of U.S. Ser. Nos. 08/497,214, 08/346,147, 08/306,511, 08/248,812, 08/227,371 and 08/154,915 (hereinafter the "priority documents") are incorporated herein by reference.

FUNDING

Work described herein was supported by National Institutes under NIH Grant Nos. R01 GM39620, R01 CA63518, R01 CA68040 of Health Grant. The United States Government has certain rights in the invention.

BACKGROUND OF THE INVENTION

Evaluating a chemical compound for its potential as a human therapeutic necessitates data and information about the compound's efficacy in an in vivo system. Ideally, the in vivo system used for data collection would be a human being; however, for ethical and pragmatic reasons, laboratory animals, and not humans, are typically used as in vivo screening systems for drug development.

Recent advances in recombinant DNA technology have enabled researchers to genetically manipulate animals, including a variety of species of rodents, livestock, birds, amphibians, insects and fish. The techniques of transgenic generation have been used to produce animals that either do not express an endogenous gene ("knock-out" or "disruptant" animals), or to produce animals that contain one or more exogenous or heterologous genes.

For instances, it has been known for sometime that it is possible to carry out the genetic transformation of a zygote (and the embryo and mature organism which result therefrom) by the placing or insertion of exogenous genetic material into the nucleus of the zygote or to any nucleic genetic material which ultimately forms a part of the nucleus of the zygote. The genotype of the zygote and the organism which results from a zygote will include the genotype of the exogenous genetic material. Additionally, the inclusion of exogenous genetic material in the zygote will result in a phenotype expression of the exogenous genetic material.

The genotype of the exogenous genetic material is expressed upon the cellular division of the zygote. However, the phenotype expression, e.g., the production of a protein product or products of the exogenous genetic material, or alterations of the zygote's or organism's natural phenotype, will occur at that point of the zygote's or organism's development during which the particular exogenous genetic material is active. Alterations of the expression of the phenotype include an enhancement or diminution in the expression of a phenotype or an alteration in the promotion and/or control of a phenotype, including the addition of a new promoter and/or controller or supplementation of an existing promoter and/or controller of the phenotype.

The genetic transformation of various types of organisms is disclosed and described in detail in U.S. Pat. No. 4,873,191, issued Oct. 10, 1989. The genetic transformation of organisms can be used as an in vivo analysis of gene expression during differentiation and in the elimination or diminution of genetic diseases.

The genetic transformation of a zygote (and the organisms which matures therefrom) is carried out by the addition of exogenous genetic material in a manner such that the exogenous genetic material becomes part of the nucleic portion of the zygote prior to a division of the zygote. If the exogenous genetic material is added after mitosis or cell division of the zygote, the exogenous genetic material must be added to each resulting nucleus. However, there is a possibility that the exogenous genetic material may not be integrated into and become a part of the genetic material of the zygote and the organism which results therefrom. Thus, the exogenous genetic material can be added to any nucleic genetic material which ultimately forms a part of the nucleus of the zygote, including the zygote nucleus.

The nucleic genetic material of the organism being transformed must be in a physical state which enables it to take up the exogenous genetic material. There are numerous ways of accomplishing this. For example, the exogenous genetic material can be placed in the nucleus of a primordial germ cell which is diploid, e.g., a spermatogonium or oogonium. The primordial germ cell is then allowed to mature to a gamete, which is then united with another gamete or source of a haploid set of chromosomes to form a zygote.

The exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote. The zygote is allowed to develop into an organism such as by implanting it in a pseudopregnant female The resulting organism is analyzed for the integration of the exogenous genetic material. If positive integration is determined, the organism can be used for the in vivo analysis of the gene expression, which expression is believed to be related to a particular genetic disease.

SUMMARY OF THE INVENTION

The present invention derives from the discovery in eukaryotic cells, particularly mammalian cells, of a novel family of cell-cycle regulatory proteins. In general, members of this family can be characterized by an amino acid sequence giving rise to a series of ankyrin-like repeats (motifs). As described herein, and in the priority documents hereto, this family of proteins function as inhibitors of cell-cycle progression, and therefore ultimately of cell growth, death and differentiation.

One aspect of the present invention relates to transgenic non-human animals having germline and/or somatic cells in which the biological activity of one or more INK4 proteins, e.g., p15, p16, p18, p19, and combinations thereof, are altered by a chromosomally incorporated transgene.

In one preferred embodiment, the transgene disrupts at least a portion of a genomic INK4 gene. For instance, the transgene may delete all or a portion of the genomic INK4 gene by replacement recombination, or may functionally interrupt one or more of a regulatory sequence or coding sequence of the genomic INK4 gene by insertion recombination.

In another preferred embodiment, the transgene encodes an INK4 protein, and expression of the transgene in cells of the transgenic animal results in altered regulation of the level of the INK4 protein relative to normal expression of the wild-type INK4 protein.

In still other preferred embodiments, the transgene encodes a mutant INK4 protein, such as dominant negative INK4 protein which antagonizes at least a portion of the biological function of a wild-type INK4 protein, or a temperature-sensitive INK4 protein which, at a nonpermissive temperature, has a reduced $K_i$ for inhibiting a CDK/cyclin kinase complex, e.g. a CDK4/cyclin or CDK6/cyclin kinase complex.

Yet another preferred transgenic animal includes a transgene encoding an antisense transcript which, when transcribed from the transgene, hybridizes with a genomic INK4 gene or a mRNA transcript thereof, and inhibits expression of the genomic INK4 gene.

In another preferred embodiment, the transgene encodes a mutant CDK4 and/or CDK6 protein which is functional in a CDK/cyclin complex but which is not inhibited by one or more INK4 proteins of the cell.

Furthermore, it is contemplates that cells of the transgenic animals of the present invention can include other transgencs, e.g., which alter the biological activity of a second tumor suppressor gene or an oncogene. For instance, the second transgene can functionally disrupt the biological activity of a second tumor suppressor gene, such as p53, DCC, $p21^{cip1}$, $p27^{kip1}$, Rb, Mad or E2F. Alternatively, the second transgene can cause overexpression or loss of regulation of an oncogene, such as ras, myc, a cdc25 phosphatase, Bcl-2, Bcl-6, a transforming growth factor, neu, int-3, polyoma virus middle T antigen, SV40 large T antigen, a papillomaviral E6 protein, a papillomaviral E7 protein, CDK4, or cyclin D1.

A preferred transgenic non-human animal of the present invention has germline and/or somatic cells in which one or more alleles of a genomic INK4 gene, e.g., a p15 gene, a p16 gene, a p18 gene, a p19 gene, and combinations thereof, are disrupted by a chromosomally incorporated transgene, wherein the transgene includes a marker sequence providing a detectable signal for identifying the presence of the transgene in cells of the transgenic animal, and replaces at least a portion of the genomic INK4 gene or is inserted into the genomic INK4 gene.

Another aspect of the present invention relates to cells and tissues isolated from the subject transgenic animals. For instance, the present invention provides composition of cells, isolated ex vivo, which include a diploid genome having a chromosomally incorporated transgene, which transgene functionally modifies the biological activity of one or more INK4 proteins. In preferred embodiments, the transgene deletes all or a portion of a genomic INK4 gene by replacement recombination, or functionally interrupts one or more of a regulatory sequence or coding sequence of the genomic INK4 gene by insertion recombination. For instance, one class of such cells contemplated by the present invention include transgenes which have (i) at least a portion of the genomic INK4 gene which directs recombination of the transgene with the genomic INK4 gene, and (ii) a marker sequence which provides a detectable signal for identifying the presence of the transgene in a cell.

The animals of this invention can be used as a source of cells, differentiated or precursor, which can be immortalized in cell culture. In a preferred embodiment, the cells are stem cells or pluripotent progenitor cells. For instance, such cells can be precursors of hematopoietic cells, neuronal cells, pancreatic cells, hepatic cells, chondrocytes, osteocytes, myocytes, or combinations thereof.

Still another aspect of the present invention relates to methods for generating nonhuman animals and stem cells having a functionally disrupted endogenous INK4 gene. In a preferred embodiment, the method comprises the steps of:

(i) constructing a transgene construct including (a) a recombination region having at least a portion of the INK4 gene, which recombination region directs recombination of the transgene with the INK4 gene, and (b) a marker sequence which provides a detectable signal for identifying the presence of the transgene in a cell;

(ii) transferring the transgene into stem cells of a non-human animal;

(iii) selecting stem cells having a correctly targeted homologous recombination between the transgene and the INK4 gene;

(iv) transferring cells identified in step (iii) into a non-human blastocyst and implanting the resulting chimeric blastocyst into a non-human female; and (v) collecting offspring harboring an endogenous INK4 gene allele having the correctly targeted recombination.

Yet another aspect of the invention provides a method for evaluating the carcinogenic potential of an agent by (i) contacting a transgenic animal of the present invention with a test agent, and (ii) comparing the number of transformed cells in a sample from the treated animal with the number of transformed cells in a sample from an untreated transgenic animal or transgenic animal treated with a control agent. The difference in the number of transformed cells in the treated animal, relative to the number of transformed cells in the absence of treatment with a control agent, indicates the carcinogenic potential of the test compound.

Another aspect of the invention provides a method of evaluating an anti-proliferative activity of a test compound. In preferred embodiments, the method includes contacting a transgenic animal of the present invention, or a sample of cells from such animal, with a test agent, and determining the number of transformed cells in a specimen from the transgenic animal or in the sample of cells. A statistically significant decrease in the number of transformed cells, relative to the number of transformed cells in the absense of the test agent, indicates the test compound is a potential anti-proliferative agent.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press:1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., New York); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental*

*Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

DETAILED DESCRIPTION OF THE INVENTION

Figure 1:
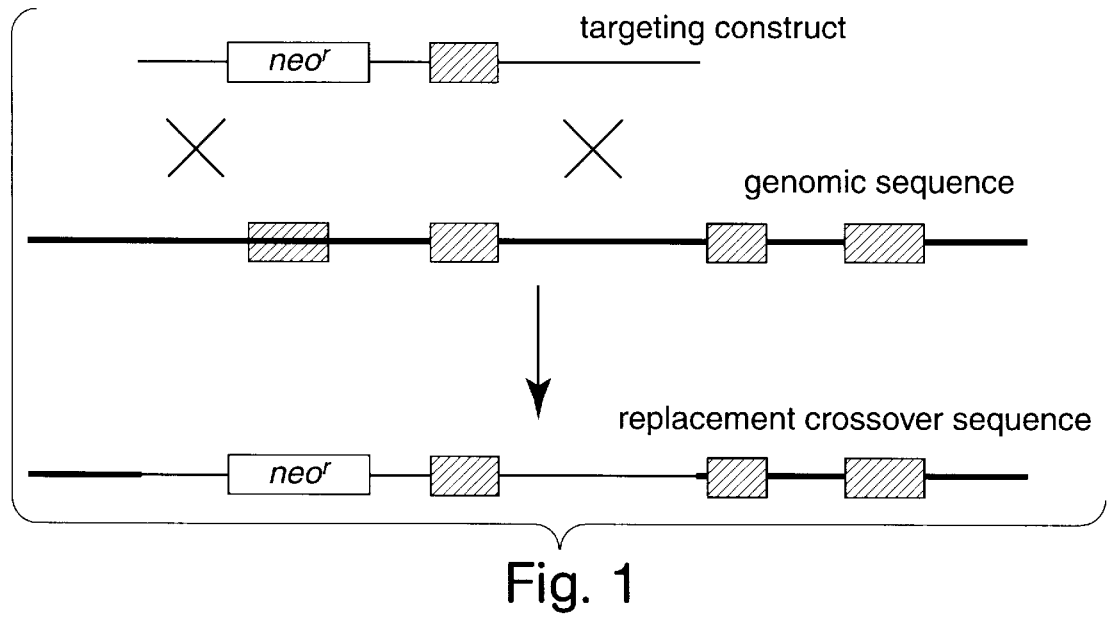
FIG. 1 shows a schematic representation of a double crossover replacement recombination event.

Cell proliferation is dependent on the sequential activation and inactivation of protein kinases, known as cyclin-dependent kinases (CDKs), at particular stages of the division cycle (reviewed in Hunter et al. (1994) *Cell* 79:573–582). Each CDK associates with a cyclin subunit which is essential for catalytic activity and probably substrate recognition. Among the members of the cyclin family, D1 (Xiong et al. (1991) *Cell* 65:691–699) was isolated as an oncogene (Motokura et al. (1991) *Nature* 350:512–515) and as a possible effector of mitogen-induced proliferation acting during the G1 phase of the cell cycle (Matsushime et al. (1991) *Cell* 65:701–713). The predominant partners of cyclin D1 are the closely related kinases CDK4 and CDK6 (Matsushime et al. (1992) *Cell* 71:323–334; Meyerson et al. (1994) *Mol. Cell. Biol.*14, 2077–2086; and Bates et al. (1994) *Oncogene*, 71–79). CDKs are subject to multiple levels of regulation including the association with inhibitory subunits (reviewed in Morgan (1995) *Nature* 374:131–134; and Sherr et al. (1995) *Genes Dev.* 9:1149–1163). One such inhibitor, p16, was first observed as a CDK4-associated protein in human cells (see U.S. Ser. No. 07/991,997; and Xiong et al. *Genes Dev.* 7:1572–1583 (1993)). The gene was subsequently isolated and shown to be a specific inhibitor of the CDK4–6/D kinases that can induce cell-cycle arrest in G1 (see U.S. Ser. Nos. 08/497,214, 08/346,147, 08/306,511, 08/248,812, 08/227,371, 08/154,915 and 07/991,997; Serrano et al. (1993) *Nature* 366:704–707; and Hannon et al. (1994) *Nature* 371:257–261). Three other members of the INK4 family have since been isolated. Each shares biochemical and biological properties with p16, including a characteristic ankyrin-like repeat motif, but are subject to different transcriptional regulation (see U.S. Ser. Nos. 08/497,214, 08/346,147, 08/306,511, 08/248,812, 08/227, 371 and 08/154,915; also subsequently reviewed in Sherr et al. (1995) *Genes Dev.* 9, 1149–1163).

The critical substrate of the CDK4–6/D kinases in vivo is the retinoblastoma-susceptibility tumor suppressor protein (Rb) (reviewed in Weinberg (1995) *Cell* 81:323–330). Rb controls passage from G1 into S-phase by sequestering transcription factors that are required for the G1/S transition. The ability of Rb to bind transcription factors is abolished by CDK phosphorylation that occurs in G1 and is sustained to the end of mitosis. Overexpression of the p16 CDK4–6 inhibitor results in cell-cycle arrest in G1 in cells with functional Rb, but is without effect in cells with inactive Rb.

The involvement of p16 in the development of human tumors was suggested by the observation that the p16 gene (called INK4a, MTS1, CDK41 or CDKN2 in the art) is mutated in many different tumor-derived cell lines and the gene maps to the chromosomal locus 9p21 (see U.S. Ser. Nos. 08/497,214, 08/346,147, 08/306,511, 08/248,812, 08/227,371, 08/154,915 and 07/991,997; as well as Kamb et al. (1994) *Science* 264:436–440; and Nobori, et al. (1994) *Nature* 368:753–756), a region which is frequently altered in human malignancies. A vast amount of data has accumulated substantiating the observations made in U.S. Ser. Nos. 08/497,214, 08/346,147, 08/306,511, 08/248,812, 08/227, 371, 08/154,915 and 07/991,997 that the loss of p16 function in the development of a wide spectrum of tumors. The mechanism of inactivation varies with the type of tumor and includes point mutation (in pancreatic esophageal carcinomas and biliary tract cancers), homozygous deletion (in non-small cell lung carcinomas, malignant gliomas, renal cell carcinomas, head and neck tumors, prostate tumors, bladder carcinomas, glioblastomas and acute lymphoblastic leukemias) and also methylation (in breast and colon cancers). Moreover, individuals inheriting a null allele of p16 are highly predisposed to the development of malignant melanoma and pancreatic cancer (Hussussian et al. (1994) *Nature Genet.* 8:15–21, Walker et al. *Human Mol. Genet.* 4:1845–1852 (1995); Goldstein et al. *New Engl J Med.* 333:970–974 (1995); Whelan et al. *New Engl. J. Med.* 333:975–977 (1995); and Gruis et al. *Nature Genet.* 10:351–353 (1995)).

In one aspect, the present invention provides a transgenic (non-human) animal in which the normal function of a cell cycle regulatory protein (herein "CCR protein" or "INK4 protein"), e.g., a protein of the p16 family, has been altered. The transgenic animal can be generated by any of a number methods. For example, the present invention contemplates transgenic animals aberrantly (over)expressing a recombinant INK4 gene in one or more cells/tissues. In other embodiments, the transgenic animal is generated by disruption of one or more alleles of an INK4 gene, or by expression of an antisense molecule, such that expression of an INK4 gene is at least partially lost in one or more cells/tissues of the animal. In yet other embodiments, the function of the INK4 protein is disrupted by mutation to a cyclin dependent kinase (CDK) which renders the CDK insensitive to the otherwise inhibitory activity of a wild-type INK4 protein.

Through manipulation of the cell-cycle circuitry, the transgenic animals of the present invention provide a means for elucidating the molecular mechanisms involved in progression of the cell cycle, and importantly, of the role of the INK4 and CDK proteins in the mechanism underlying proliferation, death and differentiation of cells. A salient feature of the subject transgenic animals derives from the use of these animals in drug discovery assays. As described in the appended examples, animals in which an INK4 gene has been disrupted are viable, but develop both spontaneous and induced tumors. Accordingly, the subject transgenic animal may be used to screen for compounds which are potential anti-proliferative agents useful for inhibiting growth of such tumors.

Another aspect of the present invention relates to cells obtained from the transgenic animal, which can be derived in culture for a variety of uses. For instance, such cell cultures will be useful for generating drug screening assays to detect compounds which offset the effect of the transgene. In other instances, such as the INK4 disruptant phenotypes, cells derived from the transgenic animal can be used to create immortalized cell lines in culture. A particularly important feature to such cells is the ability to immortalize cell lines from various developmental stages, as well as from various tissue-types. The immortalization of such cells will permit the isolation of, for example, pluripotent progenitor cells, e.g., by isolating progenitor or stem cells at various embryonic stages from transgenic animals lacking one or more functional INK4 genes.

For convenience, certain terms employed in the specification, examples, and appended claims are collected here.

The terms "INK4 protein" and "CCR protein" are used interchangeably and refer to a family of structurally related CDK inhibitors characterized by a fourfold (or greater) repeated ankyrin-like sequence (Elledge et al. (1994) Curr. Opin. Cell Biol. 6:874–878), and the ability to bind to CDKs, especially CDK4 and CDK6. Exemplary members of this protein family include p16 (INK4A/MTS1; Serrano et al (1993) Nature 366:704–707); p15 (INK4B; Hannon et al. (1994) Nature 371:257–261); p18 (Guan et al. (1994) Genes Dev. 8:2939–2952) and p19 (Chan et al. (1995) Mol. Cell Biol. 15:2682–2688; and Hirai et al. (1995) Mol. Cell Biol. 15:2672–2681). Moreover, data from hybridization and immunoprecipitation experiments indicates still other members of the INK4-protein family exist, comprising proteins representing both evolutionarily divergent sequences as well as differentially spliced variants. The diversity of members of the INK4-protein family, like the diversity of CDKs, is suggestive of individualistic roles of each member of this family, which may be tissue-type of cell-type specific, occur at different points in the cell-cycle, occur as part of different extracellular or intracellular signaling pathways, or a combination thereof.

An "INK4 gene" refers to a genomic gene structure which encodes an INK4 protein, e.g. a protein characterized by ankyrin-like repeats and binding to CDKs. An INK4 gene may further include regulatory sequences such as transcriptional regulating elements, introns, polyadenylation sites, etc.

The terms "p16 gene" and "INK4a" gene are used interchangeably herein and refer to the genomic gene encoding, among various splicing variants and reading frames, the $p16^{INK4a}$ protein. Accordingly, depending on the particular disruptant construct, the expression of one or both p16 splice variants from the INK4a gene can be disrupted, alone or in combination with the $p19^{ARF}$ protein encoded by an alternate reading frame of the INK4a gene (see Quelle et al. (1995) Cell 83: 993–1000).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid comprising an expressible nucleotide sequence. In certain embodiments, the expressible sequence includes an open reading frame encoding a polypeptide, including both exon and (optionally) intron sequences. In preferred embodiments, the nucleic acid is DNA or RNA. Exemplary recombinant genes include nucleic acids which encode all or a CDK-binding portion of an INK4 protein. Yet other exemplary recombinant genes encode a CDK4 or CDK6 mutant which has a reduced ability to bind to and be inhibited by an INK4 protein. In other embodiments, the expressible nucleotide sequence provides, upon transcription, an mRNA molecule which functions as an antisense construct, e.g. hybridizes to an INK4 gene or transcript and inhibits expression of that INK4 gene. The term "intron" refers to a DNA sequence present in a given INK4-gene which is not translated into protein and is generally found between exons.

As used herein, the term "transgene" refers to a nucleic acid sequence which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can be operably linked to one or more transcriptional regulatory sequences and any other nucleic acid, such as introns, that may be necessary for optimal expression of a selected nucleic acid. Exemplary transgenes of the present invention encode, for instance: (i) an INK4-polypeptide; (ii) a CDK mutant which is insensitive to INK4 inhibition; or (iii) an antisense transcript which inhibits expression of one or more INK4 genes in the cell in which the transgene is expressed. Other exemplary transgenes are directed to disrupting one or more genomic INK4 genes by homologous recombination with genomic sequences of an INK4 gene.

The term "transgene construct" refers to a nucleic acid which includes a transgene, and (optionally) such other nucleic acid sequences as transcriptionally regulatory sequence, polyadenylation sites, replication origins, marker genes, etc., which may be useful in the general manipulation of the transgene for insertion in the genome of a host organism.

The terms "knockout", "functionally disrupt" and "disrupting of the INK4 gene" are used interchangeably herein and refer to partial or complete loss of expression of at least a portion of an INK4 protein, or a reduction in a CDK responsiveness to an INK4 protein, in selected cells, or all of the cells of a transgenic animal.

The terms "INK4 knockout transgene", "knockout construct" and "targeting transgene construct" refer to a nucleotide sequence that decreases or suppresses expression of an INK4 protein encoded by endogenous DNA of the transgenic animal's cells. For instance, such transgene constructs can be derived to include: (i) at least one "recombination region" having a sequence that is substantially identical to or substantially complementary to an INK4 gene sequence, or sequences flanking an INK4 gene, present in a host cell of an intended transgene recipient, and (ii) a "replacement region" which becomes integrated into the host cell's genome.

The term "recombination region" refers to a segment (i.e., a portion) of a targeting transgene construct having a sequence that is substantially identical to or substantially complementary to a genomic INK4 gene sequence, or sequences flanking a genomic INK4 gene, and can facilitate homologous recombination between the genomic sequence and the targeting transgene construct.

As used herein, the term "replacement region" refers to a portion of a targeting construct which becomes integrated into an endogenous chromosomal location following homologous recombination between a recombination region and a genomic sequence.

The term "transgene expression construct" refers to a transgene construct which, when integrated into the host cell, results in expression of the transgene. "Expression" and "express" will refer to the production of a transcript, e.g., as in the case of an antisense transgene, as well as the more typical meaning in the art of transcription and translation to produce a polypeptide.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. Likewise, homology can refer to structural similarities between two polypeptides, e.g. similar domains or motifs. As used herein, a homolog of a CDK-inhibiting protein refers to a protein comprising a series of ankyrin-like repeats, e.g. four or more ankyrin-like motifs.

The term "biologically active fragment" refers to a nucleotide sequence that is less than the full-length genomic or cDNA nucleotide sequence of a gene, but which contains a sufficient portion of the full length coding sequence that the product of the fragment possesses at least a portion of the biological activity possessed by the gene product of the full length sequence.

The term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of one of the subject cell-cycle regulatory proteins, e.g. p16 or p15

"Cells" or "cell cultures" or "recombinant host cells" or "host cells" are often used interchangeably as will be clear from the context. These terms include the immediate subject cell which expresses the cell-cycle regulatory protein of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant INK4-protein.

As used herein, the term "vector" refers to a nucleic acid molecule capable of transporting another nucleic acid to which it has been linked. The term "expression vector" includes plasmids, cosmids or phages capable of synthesizing the subject INK4-protein encoded by the respective recombinant gene carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein (or antisense) coding sequences with which they are operably linked. In preferred embodiments, transcription of a recombinant INK4-gene or INK4 antisense construct is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a neuronal lineage, e.g. glial cells, or alternatively, in epithelial cells, e.g. melanocytes. In an illustrative embodiment, gene constructs utilizing nueral-specific promoters can be used as a part of gene therapy to cause expression of recombinant forms of one of the subject INK4-proteins or antisense in neuronal cells with a feature of the gene construct being a tissue-specific promoter for directing expression of the subject protein in only neuronal tissue. The term also covers so-called "leaky" promoters, which regulate expression of a selected DNA primarily in one tissue, but cause expression in other tissues as well.

The term "operably linked" refers to the arrangement of a transcriptional regulatory element relative to other transcribable nucleic acid sequence such that the transcriptional regulatory element can regulate the rate of transcription from the transcribable sequence(s).

As used herein, a "transgenic organisms" is any animal, preferably a non-human mammal, in which one or more of the cells of the animal contain heterologous nucleic acid introduced by way of human intervention, such as by trangenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of the subject INK4 proteins, e.g. either agonistic or antagonistic forms, or the transgene disrupts an endogenous INK4-gene by recombination. However, transgenic animals in which the transgene is silent are also contemplated, as for example, the FLP or CRE recombinase dependent constructs described below.

The "non-human animals" of the invention include vertebrates such as rodents, non-human primates, sheep, dog, cow, amphibians, birds, fish, reptiles, etc. The term also includes insects, such as Drosphila spp. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that the transgene is present and/or expressed in some tissues but not others.

The term "non-human mammal" refers to all members of the class Mammalia except humans.

The term "rodent" refers to all members of the phylogenetic Rodentia including any and all progeny of all future generations derived therefrom.

The term "murine" refers to any and all members of the family Muridae.

The terms "founder line" and "founder animal" refer to those animals that are the mature product of the embryos to which the transgene was added, i.e., those animals that grew from the embryos into which DNA was inserted, and that were implanted into one or more surrogate hosts.

The terms "progeny" and "progeny of the transgenic animal" refer to any and all offspring of every generation subsequent to the originally transformed mammals.

The term "naturally-occurring", as applied a CDK or INK4 gene or protein, refers to the fact that the gene or protein is identical or highly homologous with the corresponding gene or protein which exists in most animals of that species, and performs substantially the same biological function as the gene or protein occurring in such animals.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild type splicing of mRNA transcribed from the gene.

I. Transgenic Organisms

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a an INK4 protein (either agonistic or antagonistic), and antisense transcript, or a CDK4/6 mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83:9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting an INK4 gene of interest in ES cells, these changes can be introduced into the germlines of animals to generate chimeras. The gene targeting procedure is accomplished by introducing into tissue culture cells a DNA targeting construct that includes a segment homologous to a target INK4 locus, and which also includes an intended sequence modification to the INK4 genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting an INK4 gene function through the use of a targeting transgene construct designed to undergo homologous recombination with one ore more INK4 genomic sequences. As described in the appended examples, the targeting construct can be arranged so that, upon recombination with an element of an INK4 gene, a positive selection marker is inserted into (or replaces) coding sequences of the targeted INK4 gene. The inserted sequence functionally disrupts the INK4 gene, while also providing a positive selection trait. Exemplary INK4 targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line utilized in the appended examples (see also Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene (see Example, infra), the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence. Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the INK4 coding sequence, transcriptional regulatory sequence, etc. Typically, less than about 1–5 percent of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA f or the presence or absence of transcripts encoding either the gene knocked out, the marker gene, or both. In addition, Western blots can be used to assess the level of expression of the INK4 gene knocked out in various tissues of the offspring by probing the Western blot with an antibody against the particular INK4 protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of an INK4-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

Typically, crossing and backcrossing is accomplished by mating siblings or a parental strain with an offspring, depending on the goal of each particular step in the breeding process. In certain cases, it may be necessary to generate a large number of offspring in order to generate a single offspring that contains each of the knockout constructs and/or transgenes in the proper chromosomal location. For example, it may be desirable to disrupt the genes encoding p16 and p53. Thus, to generate a mouse that has both p16 and p53 knocked out, there are essentially two practical choices. First, a double knockout can be generated by injecting a single ES cell with both p16 and p53 knockout constructs, and screen for transformed cells in which both constructs integrate into the same chromosome in the same ES cell.

Alternatively, as a more preferred embodiment, two knockout animals are generated, one containing the p16 knockout construct and one containing the p53 knockout construct. These animals can then be bred together and successively interbred and screened until an offspring is obtained that contains both knockout constructs on the same chromosome (in mice, this result is obtained when a crossover event has occurred between the p16 and p15 genes since the genes encoding p16 and p53 are on the same chromosome).

In the instance of a double disruptant of the INK4a and INK4b genes in mice, the former approach of generating a single ES cell with both disruptant transgenes is preferred as the INK4a and INK4b genes are located so close to each other in the murine genome.

Exemplary transgenic crosses which can made with any of the subject INK4 transgenic animals include the progeny of mating with a second transgenic animal in which another tumor suppressor gene is functionally disrupted or in which an oncogene is overexpressed or has lost negative regulation (functionally overexpressed). For instance, the subject INK4 disruptants can be crossed with another transgenic animal (of the same species) which is disrupted at at least one locus for a tumor suppresser gene, e.g., p53, DCC, $p21^{cip1}$, $p27^{kip1}$, Rb, Mad and/or E2F. In another exemplary embodiment, the subject INK4 disruptants can be crossed with a transgenic animal which overexpresses at least one oncogene, or for which expression and/or bioactivity is deregulated for at least one oncogene, e.g., ras, myc, cdc25A or B, Bcl-2, Bcl-6, transforming growth factors (e.g., TGFα's, TGFβ's, etc.), neu, int-3, polyoma virus middle T antigen, SV40 large T antigen, one or both of the papillomaviral E6 and E7 proteins, CDK4, or cyclin D1.

In yet another embodiment, the second transgenic animal can be one in which developmental signals are altered by, e.g., disruption or overexpression of a differentiation factor, such as a TGFβ (e.g. BMPs and the like), hedgehog, dorsalin, neurotrophic factors or the like, or the functional disruption or overexpression of a receptor or signal transduction protein involved in induction of differentiation, such as a neurotrophic factor receptor, patched, TGFβ receptors (such as the activin receptor), dpc-4, WT-1 and the like.

As can be appreciated from the following, the variety of F1×F1 crosses which can be generated arises both from the effect of the transgene itself, as well as the regulation and/or pattern of defect provided by the transgene construct. For instance, the crosses can be made between homozygous or heterozygous INK4 transgenic animals and a second transgenic animal which can also be either homozygous or heterozygous. The INK4 defect of the subject transgenic animals used in the cross-breeding can be tissue-specific, developmentally specific, or ubiquitous, as can the transgenic defect of the mated second transgenic animal. For instance, when under the control of a transcriptional regulatory sequence, the transgene can be regulated in tissue-specific or ubiquitous manners. Likewise, the regulatory element can provide for constitutive expression or inducible expression. To illustrate, the INK4a disruptant described in the appended examples can be crossed with a transgenic animal comprising an activated ras oncogene driven by the Whey acidic protein (WAP) promoter. While the p16 defect will be generalized (e.g., depending on the level of mosiasism), recombinant expression of the ras oncogene will be limited principally to the mammary epithelium of the resulting cross. Such animals can be used, for example, as models for breast cancers. Alternatively, in place of the WAP-ras transgene, the INK4a disruptant can be mated with a transgenic animal expressing an oncogene under transcriptional control of a tyrosinase promoter/enhancer element. For example, the mated transgenic animal can include such oncogenes as activated ras, cyclin D1 or the CDK4 R24C mutant under transcriptional regulation of a tyrosinase promoter.

Other exemplary embodiments of genetic crosses with the subject INK4 transgenic animals include:

Cross with ζ-globin/v-Ha-ras transgenic: this transgenic expresses v-Ha-ras under the zeta-globin promoter; was developed and characterized by Leder et at., (1990) *PNAS* 87:9178–9182), and is commercially available from the Charles River Laboratory. This transgenic strain is susceptible to the development of skin papillomas and squamous cell carcinomas upon treatment of the skin with phorbol esters (a growth promoter).

Cross with MMTV/c-mvc transgenic: this transgenic expresses c-myc under the MMTCV (mouse mammary tumor virus) promoter, and was developed and characterized by Stewart et al., (1984) *Cell* 38:627–637; Sinn et al., (1987) *Cell* 49:465–475); and is commercially available from the Charles River Laboratory. This transgenic strain develops spontaneous mammary adenocarcinomas and other tumors.

Cross with Eµ-myc transgenic: this transgenic expresses c-myc under the Eµ enhancer promoter (an immunoglobulin promoter specifically expressed in lymphoid cells). This transgenic develops spontaneous B-cell lymphomas (Adams et al., (1985) *Nature* 318:533–538).

Cross with mTR transgenic: the mouse gene encoding the RNA component of the telomerase ribonucleoprotein has been cloned (Blasio et al. (1995) *Science* 269:1267–1270). Transgenic mice which overexpress MTR, or which have been disrupted for MTR expression, can be bred with the subject INK4 transgenic animals. Such genetic crosses can provide valuable information and disease models. For instance, the animals can be used to determine the effect of p16-deficiency on tumor progression (tumors may appear earlier, or they may progress to the most malignant and invasive stages faster). P16-deficiency may affect the type of tumors or their localization, and therefore they may constitute a new animal model for particular human malignancies. These animals may also constitute good animal models to assay chemotherapeutic regimes since they allow the direct comparison between various p16+ and p16− tumors phenotypes.

II. Transgene Constructs

Vectors used for transforming animal embryos are constructed using methods well known in the art, including, without limitation, the standard techniques of restriction endonuclease digestion, ligation, plasmid and DNA and RNA purification, DNA sequencing, and the like as described, for example in Sambrook, Fritsch, and Maniatis, eds., Molecular Cloning: A Laboratory Manual., (Cold Spring Harbor Laboratory Press, Cold Spring Harbor, N.Y. [1989]). Most practitioners are familiar with the standard resource materials as well as specific conditions and procedures. However, for convenience, the following paragraphs may serve as a guideline.

In one embodiment, the transgene construct used to generate the subject transgenic animals encodes an INK4 protein or a homolog thereof. The recombinant INK4 gene can be an inhibitor of cell-cycle regulation, e.g., encodes a protein which binds to an inhibits a cyclin dependent kinase in a manner similar to a wild-type INK4 protein. Alternatively, the recombinant INK4 gene can be an antagonist of the function of the wild-type INK4 protein, e.g., it may encode a protein which does not inhibit CDK activity, but which prevents inhibition of the CDK by a naturally-occurring INK4 protein, e.g., a dominant negative mutant.

Polypeptides referred to herein as having an activity of an INK4 protein preferably have an amino acid sequence corresponding to all or a portion of the amino acid sequence of the p16 protein shown in SEQ ID No. 2 or 6, of the p15 protein shown in either SEQ ID No. 4 or 8, of the p18 protein shown in SEQ ID No. 10, or the p19 protein shown in SEQ ID No. 12, or isoforms of any one of these proteins (including differential splicing variants). In preferred embodiments, the biological activity of an INK4-protein includes: an ability to regulate a eukaryotic cell-cycle, e.g. a mammalian cell-cycle; an ability to inhibit proliferation/cell growth of a eukaryotic cell, e.g. a mammalian cell; an ability to inhibit progression of a eukaryotic cell from G1 phase into S phase, e.g., inhibit progression of a mammalian cell from G1 phase into S phase, e.g., inhibit progression of a human cell from G1 phase into S phase; an ability to inhibit the kinase activity of a cyclin dependent kinase (CDK), e.g. a CDK active in G1 phase, e.g. CDK 4, e.g. CDK6; e.g. an ability to inhibit phosphorylation of a retinoblastoma (RB) or retinoblastoma-like protein by a cyclin dependent kinase. Moreover, INK4-proteins of the present invention may also have biological activities which include: an ability to suppress tumor growth, e.g. in a tumor having an unimpaired RB protein; an ability to regulate cell-cycle progression in response to extracellular factors and cytokines, e.g. functional in paracrine or autocrine regulation of cell growth and/or differentiation, e.g. inhibit CDK activation in response to transforming growth factor-β (TGF-β) or related growth, differentiation or morphogenesis factor. In this respect, the INK4-proteins of the present invention may also function to prevent de-differentiation of cells/tissue. Other biological activities of the subject INK4-proteins are described herein or will be reasonably apparent to those skilled in the art in light of the present disclosure.

In one embodiment, the transgene of the invention encodes a peptide which is an agonist or antagonist of an INK4 protein and comprises an amino acid sequence characterized by ankyrin-like repeats, e.g., four or more ankyrin-like repeats, e.g., represented in SEQ ID No. 2, 4, 6, 8, 10 or 12. Preferred nucleic acids encode a peptide having an INK4 protein activity and being at least 60% homologous, more preferably 70% homologous and most preferably 80% homologous with an amino acid sequence shown in SEQ ID No. 2, 4, 6, 8, 10 or 12. Nucleic acids which encode peptides having an activity of an INK4 protein and having at least about 90%, more preferably at least about 95%, and most preferably at least about 98–99% homology with a sequence shown in SEQ ID Nos. 2, 4, 6, 8, 10 or 12 are also within the scope of the invention. Preferably, the nucleic acid is a cDNA molecule comprising at least a portion of the coding sequence shown in SEQ ID Nos. 1, 3, 5, 7, 9 or 11. In another preferred embodiment, the INK4 protein is a dominant negative inhibitor of a wild-type INK4 protein.

In still other preferred embodiments, the INK4 protein is a temperature sensitive mutant which inhibits CDK4 and/or CDK6 at a permissive temperature, but which losses all or substantial all of its ability to inhibit such CDKs at a nonpermissive temperature. For instance, the INK4 transgene can encode an INK4 polypeptide having one or more mutations which, at higher temperatures, render the protein unstable or unable to bind a CDK relative to the naturally occurring INK4 protein.

Another aspect of the invention provides a transgene including a nucleotide sequence which hybridizes under high or low stringency conditions to a nucleic acid which encodes an INK4 polypeptide comprising ankyrin-like repeats, e.g., having all or a portion of an amino acid sequence shown in one of SEQ ID Nos. 2, 4, 6, 8, 10 or 12, e.g., hybridizes to a nucleic acid sequence designated in SEQ ID Nos. 1, 3, 5, 7, 9 or 11. Appropriate stringency conditions which promote DNA hybridization, for example, 6.0× sodium chloride/sodium citrate (SSC) at about 45° C., followed by a wash of 2.0× SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C., to high stringency conditions at about 65° C.

Transgenes which encode biologically active portions of the subject INK4 proteins are also within the scope of the invention. As used herein, a fragment of the nucleic acid encoding an active portion of an INK4 protein refers to a nucleotide sequence having fewer nucleotides than the nucleotide sequence encoding the full length amino acid sequence of, for example, the INK4 proteins represented in SEQ ID Nos. 2, 4, 6, 8, 10 or 12, and which encodes a peptide which retains at least a portion of the biological activity of the full-length protein (i.e., a peptide capable of binding a CDK) as defined herein, or alternatively, which is functional as an antagonist of the biological activity of the full-length protein.

As indicated by the examples set out below, and the priority applications, a nucleic acid encoding an INK4 protein may be obtained from mRNA or genomic DNA present in any of a number of eukaryotic cells in accordance with protocols described herein, as well as those generally known to those skilled in the art. A cDNA encoding an INK4-protein, for example, can be obtained by isolating total mRNA from a cell expressing that INK4 protein. Double stranded cDNAs can then be prepared from the total mRNA, and subsequently inserted into a suitable plasmid or bacteriophage vector using any one of a number of known techniques. A gene encoding an INK4-protein can also be cloned using established polymerase chain reaction techniques in accordance with the nucleotide sequence information provided by the invention.

Any of the methods known to the art for the insertion of DNA fragments into a vector may be used to generate transgene constructs of the present invention, including appropriate transcriptional/translational control signals and the desired INK4-encoding nucleotide sequence. See, for example, Maniatis T., Fritsch E. F., and Sambrook J. (1989): *Molecular Cloning* (*A Laboratory Manual*), Cold Spring Harbor Laboratory, Cold Spring Harbor, N.Y.; and Ausubel F. M., Brent R., Kingston R. E., Moore, D. D., Seidman J. G., Smith J. A., and Struhl K. (1992): *Current Protocols in Molecular Biology*, John Wiley & Sons, New York. These methods may include in vitro DNA recombinant and synthetic techniques and in vivo genetic recombination.

The transgenes of the present invention are typically operably linked to transcriptional regulatory sequences, such as promoters and/or enhancers, to regulate expression of the transgene in a particular manner. In certain embodiments, the useful transcriptional regulatory sequences are those that are highly regulated with respect to activity, both temporally and spatially. Thus, the promoters of choice can be those that are active only in particular tissues or cell types. The source of the promoter may be from any unicellular prokaryotic or eukaryotic organism, any vertebrate or invertebrate, or any plant. Where the promoter is obtained from a mammal, the mammal may be homologous (the same species as the mammal to be transfected) or non-homologous (a different species).

Promoters/enhancers which may be used to control the expression of the transgene in vivo include, but are not limited to, native INK4 transcriptional regulatory sequences (see, for instance, Example 1 below and Li et al. (1994) *Cancer Res* 54:6078–6082), the cytomegalovirus (CMV) promoter/enhancer (Karasuyama et al., 1989, *J. Exp. Med.*, 169:13), the human β-actin promoter (Gunning et al. (1987) *PNAS* 84:4831–4835), the glucocorticoid-inducible promoter present in the mouse mammary tumor virus long terminal repeat (MMTV LTR) (Kiessig et al. (1984) *Mol. Cell Biol.* 4:1354–1362), the long terminal repeat sequences of Moloney murine leukemia virus (MuLV LTR) (Weiss et al. (1985) *RNA Tumor Viruses*, Cold Spring Harbor Laboratory, Cold Spring Harbor, N.Y.), the SV40 early or late region promoter (Bernoist et al. (1981) *Nature* 290:304–310; Templeton et al. (1984) *Mol. Cell Biol.*, 4:817; and Sprague et al. (1983) *J Virol.*, 45:773), the promoter contained in the 3' long terminal repeat of Rous sarcoma virus (RSV) (Yamamoto et al., 1980, *Cell*, 22:787–797), the herpes simplex virus (HSV) thymidine kinase promoter/enhancer (Wagner et al. (1981) *PNAS* 82:3567–71), and the herpes simplex virus LAT promoter (Wolfe et al. (1992) *Nature Genetics*, 1:379–384).

In addition to the transgene and the transcriptional regulatory sequence, the vectors useful for preparing the transgenes of this invention typically contain one or more other elements useful for optimizing expression of the transgene in the host animal. To illustrate, the transgene construct may include transcription termination elements, such as to direct polyadenylation of an mRNA transcript, as well as intronic sequences. For example, the transgene can be flanked at its 3' end by SV40 sequences (SV40intron/pA) which add the transcription termination and polyadenylation signals to the transgene transcript. In yet other embodiments, the transgene can include intronic sequence(s) interrupting the coding sequence. In many instances, transcription of a transgene is increased by the presence of one or more introns in the coding sequence.

In still other embodiments, the transgene construct can include additional elements which facilitate its manipulation in cells (e.g., bacterial) prior to insertion in the intended recipient cell. For instance, the vector may include origin of replication elements for amplification in prokaryotic cells. Moreover, the transgene construct can include selectable markers for isolating cells, either from the recipient animal, or generated intermediate the transgenic animal (i.e., bacterial cells used for amplifying the construct). Selectable marker genes can encode proteins necessary for the survival and/or growth of transfected cells under selective culture conditions. Typical selection marker genes encode proteins that, for example: (i) confer resistance to antibiotics or other toxins, e.g., ampicillin, tetracycline or kanomycin for prokaryotic host cells, and neomycin, hygromycin or methotrexate for mammalian cells; or (ii) complement auxotrophic deficiencies of the cell.

In another embodiment, the transgene provides a CDK4 or CDK6 protein which functions in a manner similar to the naturally occurring kinase, e.g., forms cyclin/CDK kinase complexes, except that the CDK4/6 protein is insensitive to one or more INK4 proteins. As described in U.S. Ser. No. 08/497,214, we have characterized mutations to CDK4 which abrogate binding by INK4 proteins such as p15 and p16, and consequently provide kinases that are insensitive to inhibition by those INK4 proteins. These mutations, in fact, occur in stretches of amino acid residues which are conserved between CDK4 and CDK6, and presumably can be used to generate CDK6 mutants which are INK4 insensitive. Expression of such CDK4/6 mutants in a cell is the functional equivalent of disrupting expression of one or more INK4genes. Exemplary INK4 insensitive CDK4 mutants include Lys22→Ala, Arg24→Cys, and/or HVD(95–97)→FLH, each of which is described below as mutants which have lost INK4 regulation. In a preferred embodiment, a CDK4 Arg24→Cys mutant ("CDK4 R24C")of the murine CDK4 gene (SEQ ID No. 13) is provided as the transgene, either for expression with, or in place of, the wild-type CDK4. Transgene constructs for expressing CDK4 and CDK6 proteins can be generated by similar techniques as described above for transgenes encoding INK4 polypeptide.

In still another embodiment, the transcription of the transgene produces an antisense construct. As used herein, "antisense construct" refers to in situ generation of oligonucleotide probes which specifically hybridize (e.g. bind) under cellular conditions with the cellular mRNA and/or genomic DNA encoding an INK4-protein so as to inhibit expression of that protein, e.g. by inhibiting transcription and/or translation of the naturally occurring INK4 gene. The binding may be by conventional base pair complementarity, or, for example, in the case of binding to DNA duplexes, through specific interactions in the major groove of the double helix. An antisense construct of the present invention is produced by transcription of the transgene construct in the cell to produce RNA which is complementary to at least a unique portion of the cellular mRNA which encodes an INK4-protein, or which transcript can form RNA/DNA complexes with the INK4 genomic sequences.

In preferred embodiments, the transgene gives rise to a transcriptional product which specifically hybridizes to a transcript from a naturally occurring INK4 gene. For example, expression of the transgene can result in an mRNA transcript which is complementary to the mRNA transcript from a naturally occurring INK4 gene. Hybridization of the transgene transcript to the INK4 mRNA can inhibit translation of the INK4 message by, for example, disrupting the ability of ribosomes and other translational proteins to bind to the INK4 transcript. The hybridization by the transgene transcript may also destabilize the INK4 mRNA and cause more rapid turnover than otherwise would occur.

Transgene constructs for expressing antisense molecules can be generated by similar techniques as described above for transgenes encoding INK4 polypeptide or CDK4/6 mutants.

Figure 2:
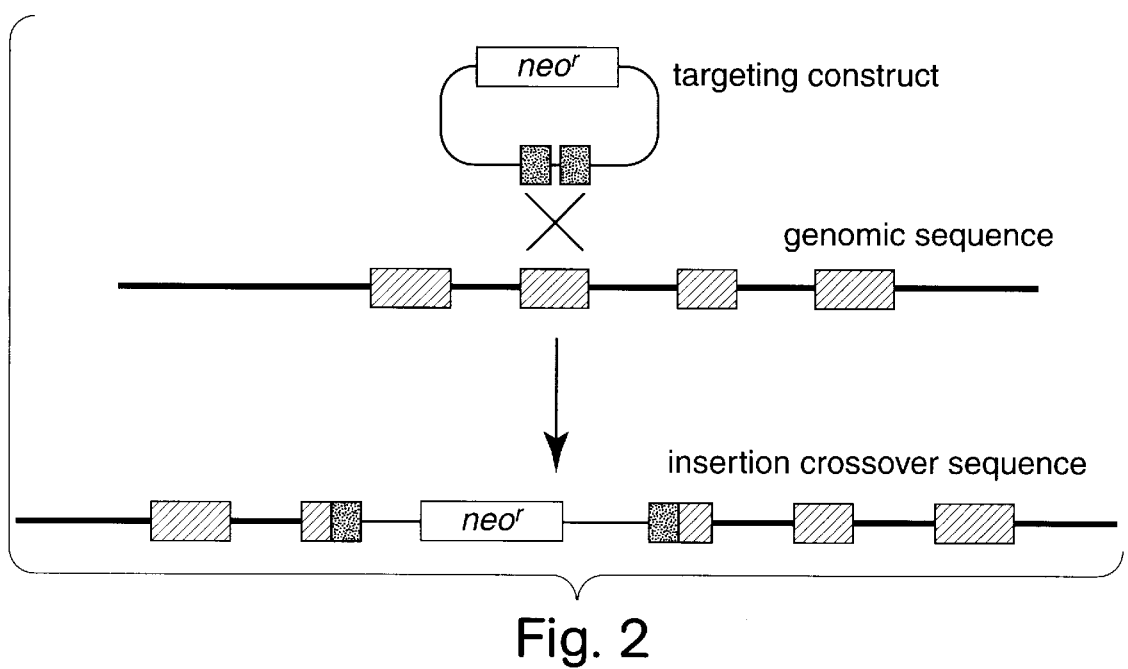
FIG. 2 shows a schematic representation of an insertion crossover recombination event.

In yet another embodiment, the transgene construct is a knockout construct. Such transgene constructs usually are insertion-type or replacement-type constructs (Hasty et al. (1991) Mol Cell Biol 11:4509). FIG. 1 shows a typical replacement-type targeting event, and FIG. 2 shows a typical insertion-type targeting event. As set out above, the transgene constructs for disruption of an INK4 gene are designed to facilitate homologous recombination with a portion of the genomic INK4 gene so as to prevent the functional expression of the endogenous INK4 gene.

In preferred embodiments, the nucleotide sequence used as the knockout construct can be comprised of (1) DNA from some portion of the endogenous INK4 gene (exon sequence, intron sequence, promoter sequences, etc.) which direct recombination and (2) a marker sequence which is used to detect the presence of the knockout construct in the cell. The knockout construct is inserted into a cell, and integrates with the genomic DNA of the cell in such a position so as to prevent or interrupt transcription of the native INK4 gene. Such insertion can occur by homologous recombination, i.e., regions of the knockout construct that are homologous to the endogenous INK4 gene sequence hybridize to the genomic DNA and recombine with the genomic sequences so that the construct is incorporated into the corresponding position of the genomic DNA. The knockout construct can comprise (1) a full or partial sequence of one or more exons and/or introns of the INK4 gene to be disrupted, (2) sequences which flank the 5' and 3' ends of the coding sequence of the INK4 gene, or (3) a combination thereof.

A preferred knockout construct will delete, by targeted homologous recombination, essential structural elements of an endogenous INK4 gene. For example, the targeting construct can recombine with the genomic INK4 gene can delete a portion of the coding sequence, and/or essential transcriptional regulatory sequences of the gene.

Alternatively, the knockout construct can be used to interrupt essential structural and/or regulatory elements of an endogenous INK4 gene by targeted insertion of a polynucleotide sequence. For instance, a knockout construct can recombine with an INK4gene and insert a nonhomologous sequence, such as a neo expression cassette, into a structural element (e.g., an exon) and/or regulatory element (e.g., enhancer, promoter, intron splice site, polyadenylation site, etc.) to yield a targeted INK4 allele having an insertional disruption. The inserted nucleic acid can range in size from 1 nucleotide (e.g., to produce a frameshift) to several kilobases or more, and is limited only by the efficiency of the targeting technique.

Depending of the location and characteristics of the disruption, the transgene construct can be used to generate a transgenic animal in which substantially all expression of the targeted INK4 gene is inhibited in at least a portion of the animal's cells. If only regulatory elements are targeted, some low-level expression of the targeted gene may occur (i.e., the targeted allele is "leaky").

The nucleotide sequence(s) comprising the knockout construct(s) can be obtained using methods well known in the art. Such methods include, for example, screening genomic libraries with INK4 cDNA probes in order to identify the corresponding genomic INK4 gene and regulatory sequences. Alternatively, where the cDNA sequence is to be used as part of the knockout construct, the cDNA may be obtained by screening a cDNA library as set out above.

In a preferred embodiment, the knockout construct is designed to under homologous recombination with an INK4 gene which encodes an INK4 polypeptide characterized by ankyrin-like repeats. For example, the knockout construct can recombine with a genomic gene encoding a p16, p15, p18 and/or p19 gene. Exemplary knockout constructs are provided by inclusion of an INK4 cDNA, e.g., of SEQ ID Nos. 1, 3, 5, 7, 9 or 11, which has been mutated to give rise to a frameshift or a premature stop codon in the coding sequence.

The knockout transgene can further include selectable markers, as described above. The proper position for the marker gene insertion is that which will serve to prevent or decrease expression of the native INK4 gene.

Furthermore, genetic techniques are known which allow for the expression of any of the above transgenes to be regulated via site-specific genetic manipulation in vivo. For instance, genetic systems are available which allow for the regulated expression of a recombinase that catalyzes the genetic recombination of a target sequence. As used herein, the phrase "target sequence" refers to a nucleotide sequence, e.g., the transgene, that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of an INK4 gene. For example, excision of a target sequence which interferes with the expression of a recombinant INK4-gene can be designed to activate expression of that gene. This interference with expression of the protein can result from a variety of mechanisms, such as spatial separation of the INK4-gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of Saccharomyces cerevisiae (O'Gorman et al. (1991) Science 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J Biol. Chem. 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation or inactivation of expression of an INK4 gene can be regulated via regulation of recombinase expression.

Use of the cre/loxP recombinase system to regulate expression of a recombinant INK4 protein requires the construction of a transgenic animal containing transgenes encoding both the Cre recombinase and the subject protein. Animals containing both the Cre recombinase and the recombinant INK4 genes can be provided through the construction of double transgenic animals. A convenient method for providing such animals is to mate two transgenic animals each containing a different transgene, e.g., an INK4-gene and a recombinase gene.

One advantage derived from initially constructing transgenic animals containing an INK4-transgene in a recombinase-mediated expressible format derives from the likelihood that certain of the INK4 transgenes will, either be overexpression of disruption, be deleterious upon to the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic p15 transgene, e.g., a p15 antisense transgene, is silent will allow the study of progeny from that founder in which disruption of cell cycle regulation by p15 in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the effect of an INK4 transgene can remain silent into adulthood until "turned on" by the introduction of the trans-activator.

III. Exemplary Use of the Transgenic Organisms

The transformed animals, their progeny, and cell lines of the present invention provide several important uses that will be readily apparent to one of ordinary skill in the art.

To illustrate, the transgenic animals and cell lines are particularly useful in screening compounds that have potential as prophylactic or therapeutic treatments of diseases such as may involve aberrant expression, or loss, of an INK4 gene. Screening for a useful drug would involve administering the candidate drug over a range of doses to the transgenic animal, and assaying at various time points for the effect(s) of the drug on the disease or disorder being evaluated. Alternatively, or additionally, the drug could be administered prior to or simultaneously with exposure to induction of the disease, if applicable.

In one embodiment, candidate compounds are screened by being administered to the transgenic animal, over a range of doses, and evaluating the animal's physiological response to the compound(s) over time. Administration may be oral, or by suitable injection, depending on the chemical nature of the compound being evaluated. In some cases, it may be appropriate to administer the compound in conjunction with co-factors that would enhance the efficacy of the compound.

In screening cell lines derived from the subject transgenic animals for compounds useful in treating various disorders, the test compound is added to the cell culture medium at the appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

Thus, the present invention provides assays for identifying agents which are either agonists (mimetics) or antagonists of the normal cellular function of one of the subject cell-cycle regulatory proteins, or of the role of an INK4-protein in the pathogenesis of normal or abnormal cellular proliferation and/or differentiation and disorders related thereto, as mediated by, for example binding of an INK4-protein to a CDK, e.g., CDK4 or CDK6.

In addition to screening a drug for use in treating a disease or condition, the transgenic animals of the present invention can also be useful in designing a therapeutic regimen aimed at preventing or curing the disease or condition. For example, the animal may be treated with a combination of a particular diet, exercise routine, radiation treatment, and/or one or more compounds or substances either prior to, or simultaneously, or after, the onset of the disease or condition. Such an overall therapy or regimen might be more effective at combating the disease or condition than treatment with a compound alone.

Agents to be tested in the animals and cell cultures of the present invention can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide, oligonucleotide, or analog thereof, having a molecular weight of less than about 2,000 daltons.

In yet another aspect of the present invention, the transgenic animals of the present invention are useful for identifying carcinogens, and evaluating their risk to humans. Currently, epidemiology and rodent bioassays are the means by which putative human carcinogens are identified. Both methods have intrinsic limitations: they are slow and expensive processes with many uncertainties. The development of methods to modify specific genes in the mammalian genome has provided promising new tools for identifying carcinogens and characterizing risk. Transgenic mice may provide advantages in shortening the time required for bioassays and improving the accuracy of carcinogen identification; transgenic mice might now be included in the testing armamentarium without abandoning the two-year bioassay, the current standard. For instance, mutagenic carcinogens can be identified with increased sensitivity and specificity using hemizygous INK4 mice in which one allele of an INK4 gene has been disrupted.

The animals of this invention can be used as a source of cells, differentiated or precursor, which can be immortalized in cell culture. Cells in which the normal function at one or more INK4 proteins is altered by a transgene may be isolated from potentially any tissue of the animal, as well as form animals at any developmental stage, e.g. embryonic to adult. The subject transgenic animals can, accordingly, be used as a source of material for the growth, identification, purification and detailed analysis of, inter alia, precursor cells, including stem cells and pluripotent progenitor cells for a variety of tissue.

In an illustrative embodiment, dissected tissue can be placed into culture, or can be further dissociated to individual cells which are subsequently cultured. As set out in the appended examples, certain of the cells obtained from animals having disrupted p16 genes were found to have gained an immortal phenotype upon culturing. In other circumstances, e.g. other of the transgenic phenotype embodiments described herein, it may be necessary to induce expression of the transgene where inducible transgenes are provided. It may also be necessary to provide a "second hit" to complete immortalization (and transformation) of the cultured transgenic cells. For instance, the second hit may be provided by treating the cells with an agent(s) which causes the cell to bypass another tumor suppressor. For instance, the cell culture media can be supplemented with caffeine, 2-aminopurine, okadaic acid, or other hypermitotic agent. In other embodiments, the second hit can be provided by transgenic expression of an oncogene or disruption of a tumor suppressor. Such cells can be derived from the progeny of crossing the subject INK4 transgenic animals with other transgenic animals as described above.

In one embodiment, disruption of an INK4 function is conditional and can be induced under cell culture conditions. For example, inducible promoters (such as IPTG-inducible promoters) can be used to conditionally control expression of a transgene providing an INK4 antisense transcript or an INK4-insensitive CDK4 or CDK6 mutant. According to such embodiments, cells isolated from these animals will have normal INK4 function. In culture, however, disruption of one or more INK4 proteins can be induced by causing expression of the transgene.

Similar embodiments are envisaged for recombinase-mediated inactivation of an INK4 gene. For instance, transgenic animals can be generated by homologous recombination to have CRE recombinase recognition sequence flanking all or a portion of an INK4 coding sequence. The progeny of this animal and another transgenic animal providing the CRE recombinase under control of an inducible promoter will provide cells whereby induction of the CRE recombinase transgene in culture will result in inactivation of the INK4 gene.

In yet another embodiment, temperature-sensitive INK4 mutants can, upon shifting to a non-permissive temperature, cause immortalization of the cultured cells.

Any of the above transgenic animals may thus provide sources of such progenitor and/or stem cells as hematopoietic progenitor cells, neuronal progenitor cells, pancreatic and/or hepatic progenitor cells, chondrocyte and/or osteocyte progenitor cells, and myocyte progenitor. The animals can also provide immortalized sources of differentiated and partially differentiated cells, such as fibroblasts, keratinocytes, etc.

Production of such cell lines may be accomplished using a variety of methods, known to the skilled artisan. The actual culturing conditions will depend on the tissue and type of cells to be cultured. Various media containing different concentrations of macro and micro nutrients, growth factors, serum, and the like, can be tested on the cells without undue experimentation to determine the optimal conditions for growth and proliferation of the cells.

EXEMPLIFICATION

The invention now being generally described, it will be more readily understood by reference to the following examples which are included merely for purposes of illustration of certain aspects and embodiments of the present invention, and are not intended to limit the invention.

U.S. patent applications U.S. Ser. Nos. 08/497,214, 08/346,147, 08/306,511, 08/248,812, 08/227,371, 08/154,915 and 07/991,997, to which the present application claims priority, teach, inter alia, the existence of a novel family of cell-cycle regulatory proteins (the "CCR proteins "or "INK4 proteins") and the importance of members of this family in the control of cell proliferation, cell death, and cell differentiation.

As described previously (see U.S. patent applications Ser. Nos. 08/154,915, 07/991,997 and 07/963,308, as well as Xiong et al. (1993) *Nature* 366:701; Xiong et al. (1993) *Genes Dev* 7:1572; Xiong et al. (1992) *Cell* 71:505; and Zhang et al. (1993) *Mol Cell Biol* 4:897), immunological procedures have been used to establish that cyclins associate, in eukaryotic cells, with a variety of potential catalytic subunits (e.g., CDKs, such as CDK2, CDK4 and CDK5). To illustrate, human cyclin D1 has been associated with a wide variety of proliferative diseases. In human diploid cells, specifically human diploid fibroblasts, cyclin D1 is complexed with a number of other cellular proteins. Among them are the catalytic subunits CDK2, CDK4 (previously called PSK-J3), CDK5 (also called PSSALRE), and CDK6 (PLSTIRE). In addition, polypeptides of 21 kDa and 36 kDa were identified in association with cyclin D1. It was shown that the 36 kDa protein is the Proliferating Cell Nuclear Antigen, PCNA. PCNA has been described as an essential accessory factor to the delta polymerase, which is required for leading-strand DNA replication and DNA repair. Cyclin D3 was also found to associate with multiple protein kinases, p21 and PCNA. It was therefore proposed that there exists a quaternary complex of D type cyclins, CDK, PCNA and p21, and that many combinatorial variations (cyclin D1, D3 with CDK2, 4, 5 and 6) may assemble in vivo.

The importance of the quaternary complex was emphasized by the discovery that cellular transformation by DNA tumor viruses is associated with selective subunit rearrangement of the cyclin D complexes, as well as other cell-cycle complexes, including cyclin A, CDC2, CDK2, CDK4 and CDK5 complexes. In particular, introduction of SV40 DNA tumor virus or its oncogenic gene product large T antigen into normal human diploid fibroblasts (HDF) causes disruption of the association between cyclin D and PCNA, CDKs (such as CDK2, CDK4, CDK5 and CDK6) and p21. For example, after dissociation from cyclin D and p21, CDK4 kinase becomes associated with a 16 kDa polypeptide (p16). Similarly, SV40 transformation causes a decrease of association of p21 with cyclin A in HDF; and adenovirus-(293 cell line) or human papilloma virus- (HeLa cell line) transformed cells, p21 is completely disassociated from cyclin A. A 19 kDa peptide, p19, then appears in a complex with cyclin A.

Thus, in many transformed cells, cyclin and CDK's associate in binary complexes which form the core of the cell-cycle regulatory machinery. In normal cells, a major fraction of the cyclin kinases acquire two additional subunits (p21 and PCNA) and thereby form quaternary complexes. Reconstitution of quaternary complexes in insect cells revealed that p21 is a universal inhibitor of cyclin kinases. As such, p21 inhibits cell-cycle progression and cell proliferation upon overexpression in mammalian cells. Taken in conjunction with the previously demonstrated absence of p21 protein in the cell-cycle kinase complexes of cells with deficient p53, these results suggest that p21 is a transcriptional target of the tumor suppressor protein, p53. One function of p53 is to act in a cellular signaling pathway which causes cell-cycle arrest following DNA damage (see for example, Kastan et al. *Cell* 71:587–597 1993). It has therefore been suggested that p21 forms a critical link between p53 and the cell-cycle control machinery.

Cyclin D/CDK4 kinase differs from the others in its inability to utilize histone H1 as a substrate. To date, the only substrates known for cyclin D/CDK4 kinases are the members of the RB family of "pocket" proteins (Matsushime et al., *Cell* 71:323–334 (1992)). Therefore, the effect of p21 was tested on the ability of cyclin D/CDK4 to phosphorylated RB. Insect cell lysates containing cyclin D or CDK4 alone showed little activity toward GST-RB. However, cyclin D/CDK4 binary complexes catalyzed substantial RB phosphorylation. Addition of increasing amounts of p21 resulted in the accumulation of cyclin D/CDK4/p21 ternary complexes with a corresponding inhibition of RB phosphorylation. Inclusion of PCNA was essentially without effect. However, cells lacking functional p53 may nevertheless retain a functional RB checkpoint which undergoes differential phosphorylation despite lack of endogenous p21.

The two-hybrid screening system (Fields et al. *Nature* 340:254 (1989)) was utilized to search for proteins that could interact with human CDK4, and more specifically, to isolate a cDNA encoding p16. Two-hybrid screening relies on reconstituting a functional GAL4 activator from two separated fusion proteins: the GAL4 DNA-binding domain fused to CDK4, GAL4db-CDK4; and the GAL4 activation domain fused to the proteins encoded by HeLa cDNAs, GAL4ad-cDNA. YPB2 was used as the recipient yeast as it is a strain that contains two chromosomal genes under the control of two different GAL4-dependent promoters: HIS3 and LacZ. YPB2 was transformed with a mixture of two plasmids encoding, respectively, the GAL4db-CDK4 and the GAL4ad-cDNA fusions; several clones were obtained that grew in the absence of histidine and that turned blue in the presence of β-gal. From DNA sequencing data it was determined that each of the positive clones derived from the same gene, although one group represented mRNAs with a shorter 3' end. The sequence of these cDNAs contained, in-phase with the GAL4ad, an open reading frame encoding a protein of 148 amino acids with a predicted molecular weight of 15,845 daltons (see SEQ ID Nos. 1 and 2). The sequence of p16 was compared by standard methods with those present in the currently available data banks and no significant homologies were found.

To test if p16 would specifically bind CDK4, YPB2 were cotransformed with the GAL4ad-p16 fusion as well as with several target GAL4db fusion constructs containing, respectively, cdc2, CDK2, CDK4, CDK5, PCNA and Snfl (a fission yeast kinase). Transformed cells were plated with and without histidine. Only the GAL4db-CDK4 fusion interacted with GAL4ad-p16 to an extent which allowed growth in the absence of histidine, indicating that this pair of fusion proteins specifically reconstituted a functional GAL4 activator able to enhance the expression of the HIS3 gene. The same result was obtained when the ability to transactivate the expression of the β-galactosidase gene was assayed.

The specificity of this interaction was further demonstrated in a cell-free system, by mixing in vitro translated ($^{35}$S)-labeled CDKs with a purified bacterially-produced fusion protein consisting of glutathione-S transferase (GST) linked to p16 (17). The GST-p16 fusion was recovered by binding to glutathione-sepharose beads and the association of each CDK was analyzed by gel electrophoresis. Consistent with the previous observations, GST-p16 bound much more efficiently to CDK4 than to cdc2, CDK2 or CDK5.

Since the predicted molecular weight of p16 is close to 16 Kd, the identity of p16 as the CDK4-associated p16 protein found in transformed cell lines (see above) was determined. Two in vitro translation products of 15 KD and 17 KD were obtained from the p16 cDNA. These products, as well as the CDK4-associated p16 protein from HeLa cells were treated with N-chlorosuccinimide. The partial NCS-proteolytic pattern of the 17 KD cDNA-derived product was very similar to the pattern obtained with the CDK4-associated p16 protein from HeLa cells, strongly suggesting that the p16 cDNA actually corresponds to p16. Partial digestion with V8 protease of the 17 KD cDNA-derived product and p16 also yielded similar patterns. It is interesting to note that the p16 protein overexpressed in insect cells has an electrophoretic mobility of 15 KD, and its NCS proteolytic map is identical to that obtained with the 15 KD cDNA derived product. This suggests that the actual p16 found in human cells and the 17 KD in vitro translation product correspond to posttranslationally modified proteins. The fact that the p16 protein overexpressed in insect cells interacts with CDK4 suggests that this modification is not essential for the interaction (see below).

The identity between p16 and the CDK4-associated protein p16 was further confirmed using antibodies raised against the purified GST-p16 fusion protein. Several human cell lines were used for this experiment: a normal cell line W138, derived from normal lung fibroblasts; the VA13 cell line derived from W138 by transformation with the SV40 T-antigen; and HeLa cells. As set out above, anti-CDK4 immunoprecipitates of W138 revealed the association of CDK4 with cyclin D1, PCNA, p21 and p16. In contrast, in VA13 and HeLa cells CDK4 is only associated with p16. Anti-p16 immunoprecipitates contained a protein with an apparent molecular weight of 16 KD which was readily detectable in the two transformed cell lines, VA13 and HeLa but to a lesser extent in the normal cell line W138. This protein not only had the same electrophoretic mobility as the p16 protein coimmunoprecipitated with anti-CDK4 serum, but also had an identical NCS partial proteolytic pattern. In addition to p16 a protein of 33Kd was observed in anti-p16 coimmunoprecipitates that was shown to be identical to CDK4 by V8-proteolytic mapping.

Northern analysis of the transcripts present in W138 and VA13 cells indicated that the p16 mRNA was around many times less abundant in W138 cells compared to VA13 cells. This difference approximately corresponded to the observed difference in the amount of p16 protein between the two cell lines, suggesting the possibility that p16 expression might be regulated at a transcriptional or post-transcriptional level. Indeed, in three non-virally transformed cell lines the expression of p16 could not be detected even after overexposure of the gel.

To study the biochemical consequences of the interaction of p16 with CDK4, active CDK4-cyclin D complexes have been reconstituted in vitro by standard protocols (Kato et al. *Genes Der* 7:331 (1993); and Ewen et al. *Cell* 73:487 (1993)). The three relevant components, CDK4, p16 and cyclin D1, were expressed in baculovirus-infected insect cells. Extracts were prepared from metabolically ($^{35}$S)-labeled insect cells that separately overexpressed p16, CDK4 or cyclin D1, as well as from cells overexpressing both CDK4 and cyclin D1. In response to increasing amounts of p16, corresponding decreases in the ability of CDK4 to phosphorylate RB was observed. This inhibition correlated with the association between p16 and CDK4 as detected by immunoprecipitation. No inhibition was observed when CDK2-cyclin D2 complexes were used in a similar assay. To confirm that the inhibition of CDK4 was due to p16, a His-tagged p16 fusion protein (His-p16) was created to have an amino terminal extension of 20 amino acids containing a tract of 6 histidine residues. This fusion protein was overexpressed in baculovirus-infected insect cells, and was purified by virtue of the high-affinity association of the histidine tract to nickel-agarose beads. The His-p16 protein preparation was shown to be >90% pure, and inhibited the activity of the CDK4-cyclin D1 complex under conditions similar to those used for inhibition by the whole lysates.

The role of the retinoblastoma gene product (RB), appears to be as a cell-cycle checkpoint which appears to at least act be sequestering transcription factors responsible for the proteins of phase. In many carcinomas, p53 function is lost by mutation or deletion. RB, on the other hand, is not apparently altered as often. However, because p16 down-regulates the CDK4/cyclin D complex, which acts to phosphorylate RB, it is proposed herein that p16 loss in certain carcinomas can alleviate the effects of the RB checkpoint and, in some manner of speaking, represent a checkpoint deficiency analogous to p53 loss. The loss of p16 would result in more effective phosphorylation of RB and hence would remove the RB-mediated inhibition of the cell-cycle. Consistent with this notion, it is described below that in a variety of human tumor cells, such as cells which overexpress a D-type cyclin, e.g. cyclin D1 or D2, the p16 gene is lost from the cell, e.g. homozygously deleted.

Moreover, the p16 gene was found to map to the human region 9p21-22, a known melanoma locus (Walker et al. (1994) *Oncogene* 9:819; Coleman et al. (1994) *Cancer Res* 54:344; Cheng et al. (1993) *Cancer Res* 53:4761; and Cannon-Albright et al. (1992) *Science* 258:1148). The chromosomal mapping was further confirmned by analysis of somatic cell hybrids through PCR amplification. Somatic hybrids containing human chromosome 9 resulted in positive PCR products being amplified.

Utilizing primers generated from the cDNA sequence of human p16 the genomic p16 gene was partially sequenced to determine intron/exon boundaries.

Genomic DNA was isolated from a variety of human tumor lines (Sambrook et al. *Molecular Cloning: A Laboratory Manual*, CSHL Press, Cold Spring Harbor, N.Y. (1989)) and was probed by PCR reactions for the presence or absence of p16 sequences. In particular, primers were used to score for exon 1 of p16, and were likewise used to detect exon 2 of p16. The p16 gene was observed to be disrupted in several tumor cell lines, confirming that p16 is indeed likely to be critical in cell transformation in certain cancerous cells. Moreover, probing of these cell lines with full length p16 cDNA (SEQ ID No. 1) demonstrated that in at least 3 of those cells apparently missing a portion of the p16 gene, the entire gene was in fact absent.

Based on immunoprecipitation experiments with anti-p16 antibodies, as well as oligonucleotide hybridization assays, it became apparent that the p16 protein represented by SEQ ID No. 2 is merely one member of a larger family of related cell-cycle regulatory proteins. For instance, even under high stringency conditions, Southern hybridization experiments of mRNA from different tissue types has indicated that approximately 4 closely related transcripts are produced. These p16 homologs, members of the INK4-protein family, may have arisen by gene duplication (e.g. each INK4-protein arises from a distinct gene) or from alternate exon splicing at the mRNA level, or a combination thereof.

Utilizing a probe consisting of the coding region of the human p16 gene, we have screened a mouse embryonal stem cell library and have isolated a genomic clone containing the coding region for a mouse homolog of the human p16 gene described above. This clone was isolated under low to moderate stringency conditions (1× SSC at 50° C.). This DNA (14kB) has been cloned in two independent pieces and the restriction map for nine restriction endonucleases has been performed. The mouse INK4-gene has been completely sequenced and the coding region provided in SEQ ID No. 5.

Moreover, utilizing degenerate probes based on the most highly conserved sequences between the human p16 clone and mouse p16 clones, a number of human and mouse p16 homologs have been isolated, such as the mouse p15 homolog (SEQ ID Nos. 7 and 8), the mouse p18 INK4 protein (SEQ ID Nos. 9 and 10), and the mouse p19 INK4 protein (SEQ ID Nos. 11 and 12).

In addition, it has been noted that TGF-β treatment causes accumulation of RB in the under-phosphorylated state and expression of RB-inactivating viral oncoproteins prevents TGF-β induced cell cycle arrest (Laiho et. al. (1990) *Cell* 62:175–185; and Pietenpol et al. (1990) *Cell* 61:777–785). While prior publications have suggested that TGF-β treatment results in down-regulation of CDK4 expression (Ewen et al. (1993) *Cell* 74:1009–1020), the data suggested to us that TGF-β might function through suppression of RB phosphorylation and pointed to the possibility that one result of TGF-β treatment might be inhibition of cyclin dependent kinases.

Accordingly, to investigate the mechanism by which TGF-β inhibits cell proliferation, we examined anti-CDK immunoprecipitates from human keratinocytes which had been arrested in G1 by exposure to TGF-β. Notably, immunoprecipitates of two G1-specific cyclin kinases, CDK4 and CDK6, contained several low molecular weight, associated proteins. These included p16 and two additional proteins of approx. 15 and 15.5 kDa. These proteins were not recovered in parallel CDC2 or CDK2 immunoprecipitates but were recovered in anti-p16 immunoprecipitates, suggesting that p15, p15.5 and p16 might be related. This was confirmed by western blotting of CDK4 and CDK6 immunoprecipitates which demonstrated that p15 and p15.5 were weakly cross-reactive with the p16 antiserum.

To isolate clones encoding putative p16 relatives, we constructed a cDNA library from TGF-β arrested HaCaT cells (Boukamp et al. (1988) *J Cell Biol* 106:761–771) and probed this library at low-stringency with the p16 coding sequence. One clone obtained in this screen encoded a 137 amino acid protein (predicted M.W. 14.7 kDa.) with homology to p16. Based upon this homology and upon biochemical properties described below, we have named this protein p15. The first 50 amino acids of p15 and p16 share approx. 44% identity. This is followed by an 81 amino acid region of approx. 97% identity after which p15 and p16 sequences diverge. The sequence of p15 can be divided into four ankyrin repeats suggesting that this structural motif is conserved in the INK4-protein family. In vitro translation of the p15 cDNA produced a protein which precisely comigrated with the p15 band present in CDK4, CDK6 and p16 immunoprecipitates from TGF-β arrested HaCaT cells. Identity of these proteins was confirmed by protease and chemical cleavage mapping.

To investigate the functional similarity of p15 and p16, we expressed p15 as a fusion protein in bacteria and tested its ability to bind and inhibit cyclin dependent kinases. p15 specifically bound CDK4 and CDK6 but did not appreciably bind CDC2, CDK2 or CDK5. To assess the consequences of binding, p15 was added to active cyclin/CDK complexes expressed in insect cells. p15 specifically inhibited the cyclin D/CDK4 and cyclin D/CDK6 enzymes but had no effect on CDK2/cyclin A kinase. Thus p15 is a functional member of the INK4-protein family. Moreover, FISH mapping of the p15 gene demonstrated that this gene lies adjacent to the p16 gene at 9p21.

While we first noted p15 in immunoprecipitates from HaCaT cells which had been arrested in G1 by serum starvation and re-stimulation in the presence of TGF-β, by comparison, we found that asynchronous, rapidly proliferating HaCaT cells contained considerably lower levels of p15 in CDK4 and CDK6 immunoprecipitates. To separate effects of TGF-β treatment from effects of G1 arrest, asynchronous cultures were treated with TGF-β for various periods, after which patterns of CDK4 and CDK6 associated proteins were examined. In as little as four hours following TGF-β addition, p15 levels rose in CDK4 and CDK6 immunoprecipitates, reaching peak levels after 6–8 hours. In contrast, CDK-associated p16 levels were unaffected by TGG-β. Northern blotting of RNA from cultures treated in parallel revealed that increased CDK4-associated p15 reflected increased abundance of p15 mRNA. In 2 hours following TGF-β treatment, p15 mRNA began to rise and reached a peak induction of approx. 30-fold after 6–8 hours. In contrast, p16 mRNA levels did not vary.

Two other mechanisms for TGF-β mediated cell cycle arrest have been previously proposed. In Mv1Lu cells, TGF-β treatment suppressed CDK4 synthesis. This was deemed causal since cells could be rendered resistant to TGF-β by constitutive overexpression of CDK4. In HaCaT cells, TGF-β treatment had no effect on CDK4 protein or mRNA levels. Based upon the properties of p15, we would predict that CDK4 overexpression could also render HaCaT cells TGF-β resistant by titrating the p15 CDK4/CDK6 inhibitor. p27, a CDK inhibitor which was purified from TGF-β arrested cells, has also been proposed as a link between TGF-β and cell cycle control. However, in HaCaT cells, TGF-β treatment had no effect on p27 mRNA levels. Thus any contribution that p27 may make to TGF-β mediated cell cycle arrest in these cells must occur by regulation at the post-translational level.

Considered together, our data suggest that p15 may function as an effector of TGF-β mediated cell cycle arrest via inhibition of CDK4 and CDK6 kinases. p15 may be the sole mediator of TGF-β induced arrest in some cells, or may cooperate with other TGF-β responsive pathways. TGF-β can regulate differentiation in some cell types, and the ability of TGF-β to affect cell cycle progression through p15 may also contribute to these processes.

Moreover, cytogenetic abnormalities at 9p21 are common in many types of human tumors suggesting the presence of a tumor suppressor gene at this locus. An inherited cancer syndrome which causes predisposition to melanoma also maps to 9p21. In addition to our data presented herein, and in U.S. Ser. No. 08/248,812 and in 08/227,371, p16 was initially proposed as a candidate for both of these activities based upon analysis of p16 deletions and point mutations in cell lines. However, the presence of a second functional member of the p16 family at 9p21 raises the possibility that loss of tumor suppression may involve inactivation of either or both genes. The response of p16 to viral oncoproteins indicates that it may function in intracellular growth regulatory pathways, while results presented here suggest that p15 may transduce extacellular growth inhibitory signals. Thus deletions of 9p21 which remove both genes (or other mutations that might inactivate both) could simultaneously negate two major proliferative control pathways. In this regard, the ability of TGF-β to induce growth arrest is reduced or lost in many neoplastically transformed cell lines. In particular, melanocytes are sensitive to growth inhibition by TGF-β, but many metastatic melanoma cells are TGF-β resistant.

Example 1

Generation of p16-deficient mice

To further explore the potential role of p16 and other INK4 proteins in both normal development and oncogenesis, we have introduced a p16-null allele into the mouse germline and generated p16-deficient mice. A murine p16 genomic fragment served as a source of p16 homologous sequences for the construction of a positive/negative replacement-type vector, p16KO, in which the p16 exons 2 and 3 were replaced with a neor cassette (see FIG. 3). p16KO was electroporated into WW6 (Loffe, E. et al. *PNAS* 92:7357–7361 (1995)) mouse embryonic stem (ES) cells and one clone was identified that contained restriction fragment length alterations consistent with disruption of the p16 gene. This ES clone was used to generate germline chimeras following microinjection into C57BL/6 blastocysts. Upon mating with C57BL/6 mice, these chimeras produced WW6/B6 F1 offspring harbouring the mutant p16 allele.

Figure 3:
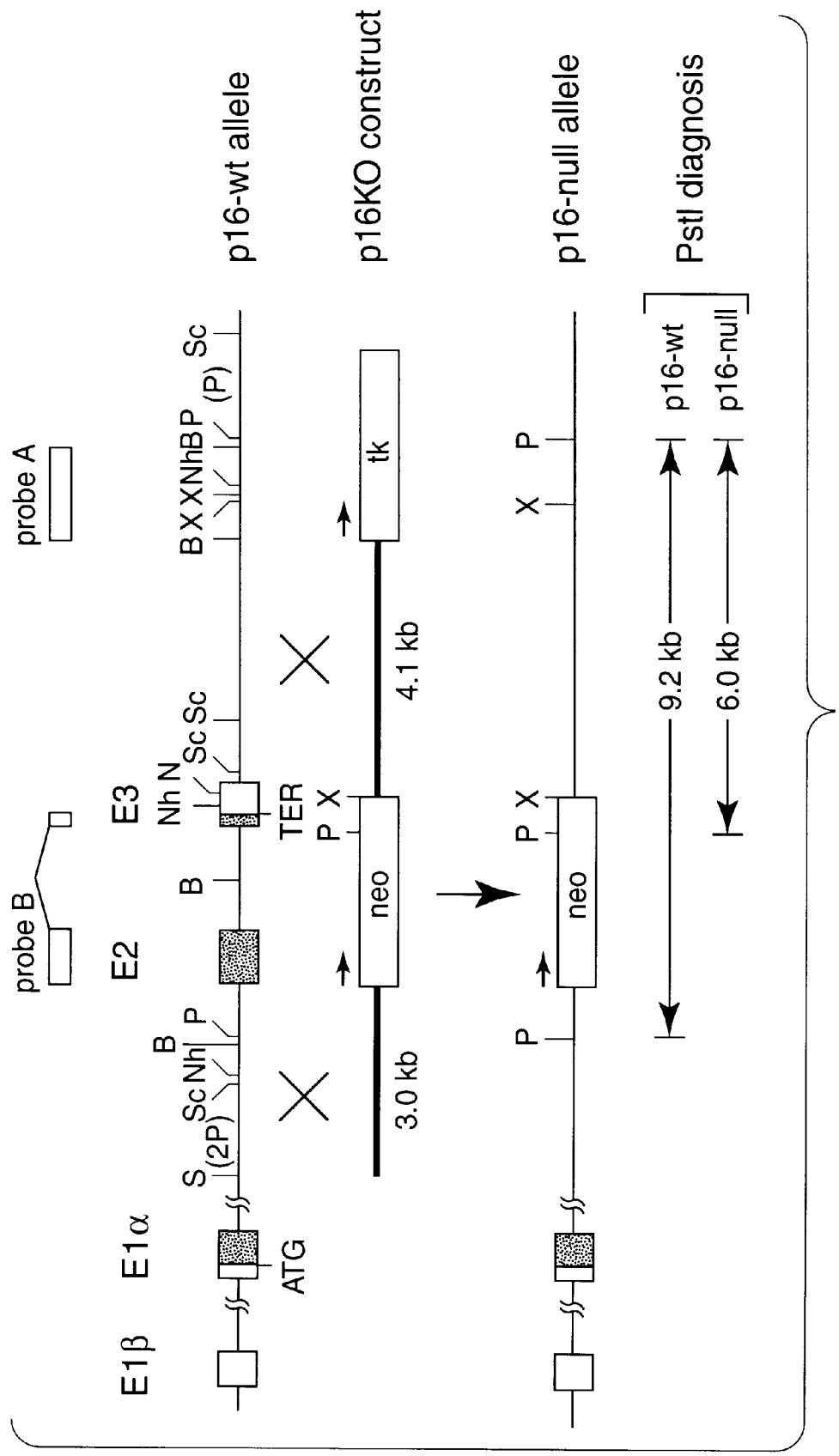
FIG. 3 shows a particular double crossover replacement recombination event for disrupting the murine p16 gene. The murine gene is divided into three exons indicated by boxes with solid areas corresponding to the coding regions. The p16-encoding exons have been named E1α, E2 and E3; an alternative exon 1, E1β, has been localized upstream of exon E1α based on the structure of the human p16 gene. The physical map for the restriction endonucleases is indicated: P=PstI, s=SalI, Sc=SacII, N=NotI , Nh=NheI, B=BamHI, X=XbaI. The precise position of 2 PstI sites in the 5'-region (2P) and 1 PstI site in the 3'-region (P) have not been determined. The targeting construct, p16KO, was derived from the pPNT vector. Homologous recombination substitutes exons 2 and 3 of the p16 allele with the pgk-neo cassette introducing the XbaI sites, and removes the TK gene.

Targeting strategy is as follows: The murine p16 gene is divided into three exons indicated by boxes with solid areas corresponding to the coding regions (see FIG. 3). The p16-encoding exons have been named E1α, E2 and E3; an alternative exon 1, E1β, has been localized upstream of exon E1α based on the structure of the human p16 gene. The physical map for the following restriction endonucleases is indicated: P: PstI; S: SalI; Sc: SacII; N: NotI; Nh: NheI; B: BamHI; X: XbaI (FIG. 3). The precise position of 2 PstI sites in the 5'-region (2P) and 1 PstI site in the 3'-region (P) have not been determined. The targeting construct, p16KO, was derived from the pPNT vector. Homologous recombination substitutes exons 2 and 3 of the p16 allele with the pgk-neo cassette introducing PstI and XbaI sites, and removes the thymidine kinase (tk) gene.

Murine p16 genomic clones were isolated by screening a mouse DE3 genomic lambda library with the human p16 cDNA. The p16KO targeting construct was electroporated into WW6 (Loffe et al. (1995) *PNAS* 92:7357–7361) embryonic stem (ES) cells and clones were selected with G418 (150 pg/ml active component) and 2 μM ganciclovir. p16+/− ES clones were identified by Southern blot analysis, and subsequently microinjected into C57BL/6 blastocysts. Resultant male chimeras with greater than 50% ES contribution as judged by coat color were mated with C57BL/6 females. Germline transmission to agouti offspring was confirmed by Southern blot analysis of tail DNA. An additional p16+/− ES clone was obtained by electroporation of E14 ES cells but the chimeras obtained did not transmit the p16-null allele to their offspring.

Southern blot of PstI-digested tail DNA from the offspring of p16+/− intercrosses. A 1.3 kb BamHI fragment (probe A) was used to identify the p16-wt and p16-null alleles, and a 0.4 kb PCR-generated probe corresponding to exons 2 and 3 (probe E.) was used as a deletion-specific probe. Southern analysis of XbaI-digested genomic DNA was consistent with the results obtained with PstI-digested DNA.

Genotype analysis of live offspring generated from heterozygous null p16 intercrosses revealed that all three genotypes were represented with a ratio close to the expected Mendelian distribution (relative ratios 1+/+:1.7+/−:1−/−, n=521). Since homozygous null p16 offspring were viable, disruption of the p16 gene was further verified at three levels. First, Southern blot analysis using a p16 cDNA probe demonstrated that p16 exons 2 and 3 were eliminated from the genome of p16−/− offspring. Second, a similar cDNA probe failed to detect p16 transcripts in total RNA derived from p16−/− embryonic fibroblasts.

Lastly, immunoprecipitation of $^{35}$S-methionine-labelled MEF lysates with anti-p16 confirmed the absence of p16 from homozygous null embryos. Briefly, p16, CDK4 and CDK6 complexes were immunoprecipitation from mouse embryo fibroblasts. Early passage p16+/+ or p16−/− MEFs were metabolically labelled with $^{35}$S-methionine and the cellular lysates were incubated with antibodies against murine p16, murine CDK4 or human CDK6 (cross-reactive with murine CDK6), in the absence or presence of a competing peptide. Immunoprecipitations were done as described in Xiong, Y., Zhang, H. & Beach, D. *Genes Dev.* 7, 1572–1583 (1993) and U.S. Ser. No. 07/991,997.

In normal cells, CDK4 is a component of at least two different multiprotein complexes: an active complex consisting of CDK4, cyclin D1, proliferating cell nuclear antigen (PCNA) and p21 (PCNA is brought into the complex through association with p21); and an inactive complex consisting of CDK4 and p16 (Serrano et al. (1993) *Nature* 366:704–707; and reviewed in Sherr et al. (1995) *Genes Dev* 7:1572–1583). These two complexes were present in anti-CDK4 immunoprecipitates from p16+/+ MEFs. In contrast, CDK4 was associated with cyclin D1, PCNA and p21, but not with p16 in p16−/− cells. Anti-CDK6 immunoprecipitates also revealed the presence of p16 in p16+/+ but not in p16−/− MEF lysates. These results confirm that the p16−/− mice do not carry the p16 gene, and that loss of p16 does not produce discernible additional changes in the composition of CDK4 and CDK6 complexes in p16−/− fibroblasts.

B. Phenotype of p16−/− mice

External examination of the p16−/− mice revealed that the p16−/− genotype cosegregates with an unusual coat pigmentation. All the p16+/+ littermates (arising from WW6/B6 intercrosses) are either black or agouti, as expected from the genetic background of the parental strains (C57BL/6 and WW6 which is ≈75% 129/Sv, ≈20% C57BL/6, and ≈5% SJL, Ioffe et al. (1995) *PNAS* 92:7357–7361). By contrast, examination of p16−/− mice (n=68) revealed that only 12% were black or agouti, and the others displayed a light-agouti color (68%) or a characteristic dark-brown color (~19%). A reduction in the amount of ocular and cutaneous pigment was also observed in most of the p16−/− mice. The mixed genetic background of the offspring analyzed (arising from WW6/B6 intercrosses) does not yet permit a precise assessment of the impact of p16 deficiency with respect to other coat colour markers.

In normal adult mice, the highest levels of p16 transcript are present in the spleen, liver and lung (Quelle et al. (1995) *Oncogene* 11:635–645). On inspection, p16−/− organs aged 2 months or younger were normal in size and appearance. However, histological analysis of the spleen revealed a mild proliferative expansion of the white pulp and the presence of numerous megakaryocytes and lymphoblasts in the red pulp. These features are consistent with an abnormal extramedullary hematopoletic process in the spleen of young p16−/− mice. In adult p16−/− mice (>6 months), extramedullary hematopoiesis becomes more severe in the spleen and is present in non-lymphoid organs such as the liver. These findings suggest that p16 could negatively regulate the proliferation of some hematopoletic lineages or their progenitors.

C. Tumour susceptibility of p16−/− mice

To directly asses the role of p16 as a tumour suppressor in vivo, litters arising from heterozygous intercrosses were randomly assigned to either untreated or carcinogen-treated groups and the rate of tumour formation was measured. In total, over 500 mice ranging in age from 1 to 9 months (>100 older than 6 months) and representing all three genotypes were monitored daily for the development of overt tumours or ill-health.

Among untreated p16−/− mice, 54% (7 of 13) developed spontaneous tumours by 8 months of age with an average latency of 6.4 months (Table 1). In contrast, none of their p16+/+ or p16+/− littermates has developed any obvious tumours or displayed compromised health after 9 months.

To compare the susceptibility of each genotype to tumour induction by carcinogens, two protocols were employed: a two-stage protocol consisting of initiation with 9,10-dimethyl-1,2-benzanthracene (DMBA) followed by promotion with ultraviolet B (280–320 nm) irradiation (UVB), or exposure to UVB alone. In the selection of these protocols, we took into account that C57BL/6 mice are poorly susceptible to the development of papillomas and squamous cell carcinomas in the skin by standard two-stage carcinogenic treatments with DMBA-initiation and phorbol esters-promotion (reviewed in DiGiovanni et al. (1991) *Prog Exp Tumor Red* 33:192–229). UVB induces a marked systemic immunosuppression in mice that is partly responsible for the carcinogenic effect of UVB (reviewed in DiGiovanni et al., supra; and Kripke et al. (1994) *Cancer Res* 54:6102–6105).

TABLE 1

Spontaneous and induced tumours in p16 deficient mice

| Mouse | Genotype | sex | Age[a] (months) | Treatment[b] | Histology[c] | Site[d] |
|---|---|---|---|---|---|---|
| 1 | −/− | M | 6.5 | none | angiosarcoma | subcutis |
| 2 | −/− | F | 6.0 | none | histiocytic giant cell sarcoma | liver |
| 3 | −/− | M | 7.5 | none | B-cell lymphoma | liver, spleen |
| 4 | −/− | F | 5.0 | none | fibrosarcoma | subcutis |
| 5 | −/− | F | 8.0 | none | B-cell lymphoma | generalized |
| 6 | −/− | F | 7.0 | none | lymphoma | generalized |
| 7 | −/− | F | 5.0 | none | fibrosarcoma | subcutis |
| 8 | −/− | F | 5.0 | UV | fibrosarcoma | subcutis, salivary gland |
| 9 | −/− | F | 4.5 | UV | squamous cell carcinoma | skin |
| 10 | −/− | M | 8.0 | UV | lymphoma | intestine |
| 11 | −/− | M | 8.0 | UV | fibrosarcoma | subcutis |
| 12 | −/− | F | 7.0 | UV | lymphoma | intestine |
| 13 | −/− | M | 7.0 | UV | lymphoma | intestine |
| 14 | −/− | F | 2.5 | DMBA + UV | fibrosarcoma | subcutis × 2 |
| 15 | −/− | F | 2.5 | DMBA + UV | fibrosarcoma | subcutis × 2 |
| 16 | −/− | M | 2.0 | DMBA + UV | B-cell lymphoma | generalized |
| 17 | −/− | M | 2.5 | DMBA + UV | fibrosarcoma | subcutis × 3 |
| 18 | −/− | F | 2.0 | DMBA + UV | B-cell lymphoma | generalized |
| 19 | −/− | M | 1.5 | DMBA + UV | fibrosarcoma | subcutis × 2 |
| 20 | −/− | M | 2.8 | DMBA + UV | fibrosarcoma | subcutis × 2 |
| 21 | −/− | F | 1.5 | DMBA + UV | fibrosarcoma | subcutis |
| 22 | −/− | M | 2.5 | DMBA + UV | lymphoma | generalized |
| 23 | +/− | F | 1.5 | DMBA + UV | B-cell lymphoma | generalized |
| 24 | +/− | F | 4.2 | DMBA + UV | low grade fibrosarcoma | subcutis |
| 25 | +/− | M | 5.0 | DMBA + UV | squamous cell carcinoma | skin |
| 26 | +/− | F | 5.0 | DMBA + UV | fibrosarcoma | subcutis |
| 27 | chimera | M | 1.0 | none | teratoma | subcutis |

[a]Age at the time of tumour detection or death
[b]See Methods for details about treatments
[c]Histological characterization of the tumours
[d]Numbers in parentheses indicate number of tumours Methods for Table 1:
Litters generated from p16+/− intercrosses were subjected to two different treatments: DMBA plus UVB exposure; and UVB exposure only. DMBA treatment consisted on a single application of 50 μl of a solution 0.5% DMBA (Sigma) in acetone applied to the dorsal surface on postnatal day 1 to 5. The UVB source were 2 FS-20T12/UVB bulbs (National Biological Corp.) with emission peaks at 295 mn, 305 nm and 310 nm. Irradiance of UVB bulbs was measured prior to each treatment with a photometer calibrated to 310 nm. UVB treatment consisted of three exposures per week beginning on postnatal day 4 to 8. Animals were initially exposed to an UVB dose of 100 mJ/cm$^2$ per session (a dose that was determined to be equivalent to minimal erythema dose for newborn mice). Dosage was incremented by 10% per treatment unless erythema or scaling was noted. On average, animals were exposed to ~27 UVB sessions, with maximum UVB dose set at 700 mJ/cm$^2$. Dorsal surface of all animals was shaved weekly. For histological analysis of the spontaneous tumours developed in p16−/− mice, photomicrographs of sections of a subcutaneous tumour were processed as follows: hematoxylin and eosin staining; negative immunohistochemical staining against the melanocyte-marker protein S-100; note the positive staining of a peripheral nerve; positive immunohistochemical staining against vimentin; note the staining of some invaded muscle fibres. Likewise, photomicrographs of sections of a lymph node processed as follows: hematoxylin and eosin staining; positive immunohistochemical staining against the leukocyte surface-marker CD45; positive immunohistochemical staining against the B-cell surface-marker B220. In all cases, diaminobenzadine was used as the chromogen and sections were counterstained with hematoxylin.

In the DMBA/UVB treated cohort, 43% (9 of 21) of p16−/− mice developed highgrade malignant tumours with an average latency of 2.2 months after the treatment was initiated at 1 week of age (Table 1). In comparison, only 14% (4 of 28) of the p16+/− littermates developed slow-growing tumors after 3.9 months. None (n=24) of the p16+/+ mice, ranging in age from 2.5 to 6 months, developed any tumour. The group of p16−/− mice treated with UVB alone developed tumours in 29% (6 of 21) of the mice with an average latency of 6.6 months. This latency is identical to that of spontaneous tumour development and it is, therefore, unclear that UVB alone has any effect. All of the UVB-treated p16+/+ (n=31) or p16+/− (n=49) littermates, ranging in age from 3 to 7.5 months, are free of detectable tumours. Together, these results directly demonstrate that the absence of p16 results in increased susceptibility to the development of cancers.

At the histopathological level, p16−/− mice develop two major tumour types. One, arising in the subcutis and invading the underlying musculature, is composed of anaplastic spindle cells with frequent mitotic Figures. Since these features are consistent with either melanoma, leiomyosarcoma or fibrosarcoma, we have further defined their histogenesis with a battery of immunohistochemical markers. Tumour cells did not show immunoreactivity to antibodies against either protein S100, a melanocyte marker protein, or desmin. These results indicate that the tumours are not melanoma or myogenic sarcoma, respectively. However, cells were positive for vimentin, thus favouring the diagnosis of fibrosarcoma. Another type of vimentin-positive sarcoma showed characteristic features of a highly vascularized angiosarcoma with neoplastic cells in the lumina of ill-defined vessels forming communicating channels. The second major histological tumour category exhibited a more generalized distribution and primarily involved lymphoid organs. The normal architecture of the affected lymph nodes was completely effaced by small round cells with hyperchromatic nuclei, prominent nucleoli, scanty cytoplasm, and numerous and bizarre mitotic Figures. These tumour cells displayed positive immunostaining with anti-CD45 and B220 antibodies, but were unreactive with anti-CD3, establishing the diagnosis of B-cell lymphoma. The spectra of tumour types arising in untreated animals and in carcinogen-treated animals were similar, although two p16−/− mice exposed to UVB alone or to DMBA/UVB, developed cutaneous lesions that proved to be well-differentiated squamous cell carcinomas. In summary, absence of p16, in mice of the genetic background described, results in susceptibility to the development of lymphomas and sarcomas.

D. Growth properties of p16−/− MEFs

Two observations point to a role for p16 as a regulator of normal fibroblast growth. First, p16-deficient mice develop fibrosarcomas with high frequency (see Table 1) and, second, p16 appears to be the major INK4 protein associated with CDK4 and CDK6 in normal mouse embryonic fibroblasts. Accordingly, we have studied the behaviour of primary mouse embryo fibroblasts (MEFs) derived from individual embryos. Early pasage p16−/− MEFs grew significantly faster than similarly passaged p16+/+ and p16+/− MEFs (about 3 times faster). All cultures were morphologically indistinguishable and were susceptible to arrest by contact inhibition. However, monolayers formed by p16−/− MEFs achieved higher cellular densities compared to p16+/− or p16+/+ MEFs (about 3 times higher, p16−/− MEF density at confluency $2\times10^5$ cells/cm$^2$). In addition, normal primary MEFs initially grow at a constant rate until they enter a slow-growth phase, or senescence, after approximately 10 population doublings (10 PDL) (R öhme et al. (1981) *PNAS* 78:5009–5013). Nevertheless, spontaneous escape from senescence occurs in normal rodent cells (frequency ~$2\times10^{-6}$) (Kraemer et al. (1986) *J Natl Cancer Inst* 76:703–709). p16−/− MEFs formed colonies much more efficiently (~10 times) than p16+/+ MEFs, suggesting that the p16−/− cells undergo spontaneous immortalization more easily than do the p16+/+ cells. Thus, serial culture of p16−/− MEFs resulted in a constant and rapid growth rate with no detectable senescent phase, while p16+/+ and p16+/− MEFs entered into a slow-growth phase of variable duration after 8–16 population doublings. Together, these observations suggest that loss of p16 facilitates cellular immortalization.

E. Susceptibility of p16−/− MEFs to neoplastic transformation

Neoplastic transformation of primary rodent cells requires the cooperation of pairs of oncogenes, reflecting the necessity to disregulate cell proliferation minimally at two different levels (Land et al. (1983) *Nature* 304:596, and reviewed in Hunter et al. (1991) *Cell* 64:249–270). Compared to rat cells, neoplastic transformation of mouse embryo fibroblasts occurs infrequently and has been observed only with particular pairs of cooperating oncogenes (e.g. Ha-ras$^{val12}$/E1a and Ha-ras$^{val12}$/CDC25A; Galaktionov et al. (1995) *Science* 269:1575–1577 and Palmieri et al. (1989) *Curr Topics Microbiol Immunol* 148:43–91; neoplastic transformation of MEFs by Ha-ras$^{val12}$/myc has not been reported; see also reviews Palmieri et al., supra and Ruley et al. (1990) *Cancer Cells* 2:258–268).

In order to determine the susceptibility to neoplastic transformation of p16−/− MEFs, the following foci-formation assays were performed. Early-passage MEFs (PDL≦9) derived from individual embryos were seeded ($10^6$ cells) in plates of 10 cm diameter and grown in DMEM plus 10% fetal bovine serum (FBS) over-night. The medium was changed 4 hours before transfections began. Transfections were done by standard calcium-phosphate procedures with DNA mixtures containing 10 µg Of each of the relevant plasmids plus the corresponding amount of carrier DNA plasmid for a total of 30 µg DNA. After 8 h of incubation with the precipitates, the incubation medium was changed and cultures were fed with fresh medium every three days. At day 14 post-transfection, cells were fixed and stained with Giemsa, and foci were scored visually. For colony-formation in soft-agar, cells were plated into soft-agar (0.3%) containing DMEM plus 10% FBS for 3 weeks.

For tumour formation in nude mice, 106 cells derived from a p16(−/−)/Ha-ras$^{Val12}$ focus randomly chosen were injected into each of the two flanks of three nude mice. Tumour formation was scored after 3 weeks. Nude mice were obtained from the Jackson Laboratory.

As anticipated, cotransfection of Ha-ras$^{val12}$ and myc into presenescent (PDL≦9) p16+/+ or p16+/− MEFs failed to produce transformed foci (Table 2). Interestingly, focus formation was observed in the p16−/− monolayers after transfection of Ha-ras$^{val12}$ alone (Table 2). Transfection with myc alone neither yielded foci, nor increased the ability of Ha-ras$^{val12}$ to transform p16−/− MEFs (Table 2). Transfection of activated raf (raf-bxb; Bruder et al. (1992) *Genes Dev* 6:545–556) alone into p16−/− MEFs produced foci with an efficiency comparable to that of Ha-ras$^{val12}$, whereas transfection of p16+/+ MEFs with raf-bxb did not generate foci. The tumorigenicity of the ras-transformed p16−/− foci was further demonstrated by their anchorage-independent growth, and also by their ability to produce tumours in nude mice. These results indicate that p16-deficiency can cooperate with activated Ha-ras alone to effect malignant transformation of primary fibroblasts, and further suggests that loss of p16 may represent an immortalization event in the transformation of primary fibroblasts.

TABLE 2

Neoplastic transformation of p16+/+, p16+/− and p16−/− MEFs

| Assay[a] | Transfected DNA[b] | Number of foci[d] p16 genotype | | |
|---|---|---|---|---|
| | | +/+ | +/− | −/− |
| 1 | carrier plasmid | 0 | 0 | 0 |
| | c-myc | 0 | 0 | 0 |
| | Ha-ras$^{Val12}$ | 0 | 0 | 27 |
| | Ha-ras/c-myc | 0 | 0 | 22 |
| 2 | carrier plasmid | 0 | n.d.[e] | 0 |
| | Ha-ras$^{Val12}$ | 0 | n.d. | 26 |
| | Ha-ras$^{Val12}$ | 0 | n.d. | 32 |
| | Ha-ras$^{Val12}$ [c] | 0 | n.d. | 7 |
| 3.1 | carrier plasmid | 0 | 0 | 0 |
| | Ha-ras$^{Val12}$ | 0 | 0 | 8 |
| 3.2 | carrier plasmid | 0 | 0 | 0 |
| | Ha-ras$^{Val12}$ | 0 | 0 | 25 |

[a]The following cultures were used in each assay (abbreviations: wt = p16+/+; sko = p16+/−; dko = p16−/−):
Assay 1: wt-7, sko-1, dko-6.
Assay 2: wt-4, dko-6.
Assay 3.1: wt-3, sko-1, dko-6.
Assay 3.2: wt-8, sko-12, dko-10.
Assays 3.1 and 3.2 were done simultaneously
[b]The following plasmids were used:
pNV-Ha-ras encoding human c-HaRas(G12V) under the murine leukemia virus long terminal repeat (LTR);
pSVv-myc encoding avian MC29 virus myc under its own LTR;
an unrelated yeast plasmid, vector pOAD-GL, was used as carrier DNA
[c]In this particular case, c-Ha-Ras(G12V) was encoded by plasmid pDCR-rasV12
[d]Foci generated after transfection of an initial population of 106
[e]n.d. = not done F. Discussion of Transgenic Mice The hypothesis that p16 is a tumour suppressor is based on several existing lines of evidence. p16 negates the activity of a known oncogene, cyclin D1, has the capacity to arrest cell proliferation. The p16 gene is frequently inactivated in a variety of human cancers, and inherited mutant alleles of p16 segregate with susceptibility to the development of malignant melanoma and pancreatic adenocarcinoma. Through the generation of homozygous null p16 mice by gene targeting, we provide direct evidence that p16-deficiency facilitates tumour development in a mammalian organism.

Loss of p16 function does not result in gross congenital defects indicating that p16 is not essential for viability or organo-morphogenesis. In accord with our findings, two cases of a p16$^{null}$/p16$^{null}$ genotype have been reported in humans without attendant developmental effects (Gruis et al. (1995) Nature Genet 10:351–353). The p16−/− mice have a unique coat color, and a reduction in cutaneous and ocular pigmentation compared to their p16+/+ and p16+/− littermates. This suggests a potential role for p16 in melanocyte growth or differentiation. In this regard, it is notable that transgenic mice expressing the SV40 large T-antigen under the tyrosinase promoter also have decreased coat color pigmentation (Bradl et al. (1991) PNAS 88:164–168), and also that melanocytes transformed with a number of oncogenes show hypopigmentation (Dotto et al. (1989) J Cell Biol 109:3115–3128; and Wilson et al. (1989) Cancer Res 49:711–716).

Young p16−/− mice (about 2 months old) display enlargement of the splenic white pulp and the presence of lymphoblasts and megakaryocytes in the red pulp, consistent with abnormal extramedullary hematopoiesis. This process becomes more severe in the spleen of older mice (>6 months) and affects non-lymphoid organs as the liver. These observations suggest that p16 may normally regulate the proliferation of some hematopoietic lineages or their progenitors. By comparison, Rb-deficient mice die during embryonic development with a severe impairment in the production of mature enucleated erythrocytes and, in some cases, an increase in liver megakaryocyte and myeloid cell numbers (Lee et al. (1992) Nature 359:288; Jacks et al. (1992) Nature 359:295; and Clarke et al. (1992) Nature 359:328).

The p16−/− mice develop spontaneous tumours at an early age (52% of the mice before reaching 8 months of age) and, compared to their p16+/+ littermates, are extremely susceptible to the development of tumours following carcinogenic treatments (DMBA/UVB; and UVB alone). Most of the tumours in the p16−/− mice correspond to soft-tissue sarcomas and B-cell lymphomas. This pattern is reminiscent of the p53-deficient mice which develop mostly thymic lymphomas (~75%) and osteosarcomas (Donehower et al. (1992) Nature 356:215). Preference in the development of lymphomas may be related to the intrinsic propensity of C57BL mouse strains to develop lymphomas rather than other malignancies (3–10 times higher incidence; Drinkwater et al. (1991) Prog Exp Tumor Res 33:1–20). Inactivation of the p16 gene is common in human lymphomas (Hirama et al. (1995) Blodd 86:841), but rare in human sarcomas, at least as estimated by the frequency of homozygous deletions (Maelandsmo et al. (1995) Br J Cancer 72:393). The absence of skin melanomas among the p16-deficient mice might be explained by a longer latency period, but, in general, mice are poorly susceptible to the development of cutaneous melanoma (DiGiovanni et al., supra).

At the cellular level, p16-deficiency resulted in altered cell growth properties. p16−/− cells are either immortal or can be spontaneously immortalized at a higher frequency than p16+/+ or p16+/− cells, suggesting a role for p16 normally in establishing replicative senescence. Moreover, primary p16−/− cells can be neoplastically transformed by introduction of activated Ha-ras alone, a property that is characteristic of immortal rodent cell lines (Land et al. (1983) Nature 304:596–602; Hunter, supra; Palmieri et al., supra; Ruley et al. (1990) Cancer Cells 2:258; and Newbold et al. (1983) Nature 304:648). The immortal phenotype of the p16−/− cells may explain the consistent observation that p16 gene inactivation is more common in tumour cell lines than in the corresponding human tumours and is presumably selected in vitro (reviewed in Hirama et al. (1995) Blood 86:841).

The p16 and cyclin D1 proteins are, respectively, negative and positive regulators of the CDK4 kinase which, in turn is responsible for the phosphorylation and inactivation of Rb. Therefore, two tumour suppressors, p16 and Rb, and two inducers of proliferation, CDK4 and cyclin D1, are functionally related in a single regulatory pathway. In many tumour types, genetic alteration of one component of this pathway occurs in exclusivity with respect to the alteration of other components. Thus, inactivation of p16 or Rb, or amplification of CDK4 or cyclin D1 has been reported in tumour-derived cell lines, lung tumours, glioblastomas, sarcomas and esophageal cancers, but alteration of one gene is inversely correlated with dysfunction of any other (Maelandsmo et at, supra; Shapiro et al. (1995) *Cancer Res* 55:505–509; Schmidt et al. (1994) *Cancer Res* 54:6321; He et al. (1995) *Cancer Res* 55:4833; Okamaoto et al. (1994) *PNAS* 91:11045; and Jiang et al. (1993) *PNAS* 90:9026). This pattern of genetic alterations thus suggests that the p16/CDK4/D1/Rb pathway behaves as a single genetic target in oncogenic transformation. The results presented in this application directly demonstrate that p16 is a tumour suppressor and support the notion that p16 inactivation is an important genetic lesion in the development of human cancers.

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A transgenic mouse having germline and somatic cells comprising a chromosomally incorporated transgene that disrupts the genomic p16$^{INK4a}$ gene and inhibits expression of said gene, wherein said disruption comprises insertion of a selectable marker sequence resulting in said transgenic mouse exhibiting increased susceptibility to the formation of tumors as compared to the wildtype mouse.

2. The transgenic mouse of claim 1, wherein the germline and somatic cells of the transgenic mouse further comprise a second transgene which disrupts a second endogenous tumor suppressor gene and inhibits expression of said second tumor suppressor gene.

3. The transgenic mouse of claim 1, wherein said mouse is homozygous for said disruption.

4. The transgenic mouse of claim 1, wherein said mouse is heterozygous for said disruption.

5. The transgenic mouse of claim 1, wherein the germline and somatic cells of the transgenic mouse further comprises a second transgene comprising an oncogene, operably linked to a promoter wherein said transgene is expressed.

6. A transgenic mouse having germline and somatic cells in which at least one allele of a genomic $p16^{INK4a}$ gene is disrupted by a chromosomally incorporated transgene, which transgene inhibits the expression of said genomic $p16^{INK4a}$ gene, wherein (i) said genomic $p16^{INK4a}$ gene encodes a p16 protein comprising ankyrin repeats and which p16 protein specifically binds to CDK4 or CDK6, and (ii) said disruption comprises insertion of a selectable marker sequence, which replaces all or a portion of the genomic $p16^{INK4a}$ gene or is inserted into the coding sequence of said genomic $p16^{INK4a}$ gene and (iii) said transgenic mouse has increased susceptibility to the development of neoplasms.

7. Isolated mammalian cells comprising a diploid genome including a chromosomally incorporated transgene, which transgene disrupts the genomic $p16^{INK4a}$ gene and inhibits expression of said gene.

8. The cells of claim 7, which cells are mouse cells.

9. A method for generating a mouse and mouse embryonic stem cells having a functionally disrupted endogenous $p16^{INK4a}$ gene, comprising the steps of:

(i) constructing a transgene construct including (a) a recombination region having all or a portion of the endogenous $p16^{INK4a}$ gene, which recombination region directs recombination of the transgene with the endogenous $p16^{INK4a}$ gene, and (b) a marker sequence which provides a detectable signal for identifying the presence of the transgene in a cell;

(ii) transferring the transgene into embryonic stem cells of a mouse;

(iii) selecting embryonic stem cells having a correctly targeted homologous recombination between the transgene and the $p16^{INK4a}$ gene;

(iv) transferring said cells identified in step (iii) into a mouse blastocyst and implanting the resulting chimeric blastocyst into a female mouse; and (v) selecting offspring harboring an endogenous $p16^{INK4a}$ gene allele comprising the correctly targeted recombination.

10. A method of evaluating the carcinogenic potential of an agent comprising (i) contacting the transgenic mouse of claim 1 with a test agent, and (ii) comparing the number of transformed cells in a sample from the treated mouse with the number of transformed cells in a sample from an untreated transgenic mouse or transgenic mouse treated with a control agent, wherein the difference in the number of transformed cells in the treated mouse, relative to the number of transformed cells in the absence of treatment or treatment with a control agent, indicates the carcinogenic potential of the test compound.

11. A method of evaluating an anti-proliferative activity of a test compound, comprising:

(i) providing a transgenic mouse of claim 1 having germline and somatic cells in which the expression of the $p16^{INK4a}$ gene is inhibited by said chromosomally incorporated transgene, or a sample of cells derived therefrom;

(ii) contacting the transgenic mouse or the sample of cells with a test agent; and (iii) determining the number of transformed cells in a specimen from the transgenic mouse or in the sample of cells, wherein a statistically significant decrease in the number of transformed cells, relative to the number of transformed cells in the absence of the test agent, indicates the test compound is a potential anti-proliferative agent.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 994 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 41..508

(xi) SEQUENCE DESCRIPTION: SEQ ID NO:1:

```
CGGAGAGGGG GAGAACAGAC AACGGGCGGC GGGGAGCAGC ATG GAT CCG GCG GCG        55
                                            Met Asp Pro Ala Ala
                                              1               5

GGG AGC AGC ATG GAG CCT TCG GCT GAC TGG CTG GCC ACG GCC GCG GCC       103
Gly Ser Ser Met Glu Pro Ser Ala Asp Trp Leu Ala Thr Ala Ala Ala
             10                  15                  20

CGG GGT CGG GTA GAG GAG GTG CGG GCG CTG CTG GAG GCG GTG GCG CTG       151
Arg Gly Arg Val Glu Glu Val Arg Ala Leu Leu Glu Ala Val Ala Leu
         25                  30                  35

CCC AAC GCA CCG AAT AGT TAC GGT CGG AGG CCG ATC CAG GTC ATG ATG       199
Pro Asn Ala Pro Asn Ser Tyr Gly Arg Arg Pro Ile Gln Val Met Met
     40                  45                  50

ATG GGC AGC GCC CGA GTG GCG GAG CTG CTG CTG CTC CAC GGC GCG GAG       247
Met Gly Ser Ala Arg Val Ala Glu Leu Leu Leu Leu His Gly Ala Glu
 55                  60                  65

CCC AAC TGC GCC GAC CCC GCC ACT CTC ACC CGA CCC GTG CAC GAC GCT       295
Pro Asn Cys Ala Asp Pro Ala Thr Leu Thr Arg Pro Val His Asp Ala
 70                  75                  80                  85

GCC CGG GAG GGC TTC CTG GAC ACG CTG GTG GTG CTG CAC CGG GCC GGG       343
Ala Arg Glu Gly Phe Leu Asp Thr Leu Val Val Leu His Arg Ala Gly
                 90                  95                 100

GCG CGG CTG GAC GTG CGC GAT GCC TGG GGC CGT CTG CCC GTG GAC CTG       391
Ala Arg Leu Asp Val Arg Asp Ala Trp Gly Arg Leu Pro Val Asp Leu
            105                 110                 115

GCT GAG GAG CTG GGC CAT CGC GAT GTC GCA CGG TAC CTG CGC GCG GCT       439
Ala Glu Glu Leu Gly His Arg Asp Val Ala Arg Tyr Leu Arg Ala Ala
            120                 125                 130

GCG GGG GGC ACC AGA GGC AGT AAC CAT GCC CGC ATA GAT GCC GCG GAA       487
```

```
Ala Gly Gly Thr Arg Gly Ser Asn His Ala Arg Ile Asp Ala Ala Glu
    135                 140                 145

GGT CCC TCA GAC ATC CCC GAT TGAAAGAACC AGAGAGGCTC TGAGAAACCT          538
Gly Pro Ser Asp Ile Pro Asp
150                 155

CGGGAAACTT AGATCATCAG TCACCGAAGG TCCTACAGGG CCACAACTGC CCCCGCCACA     598

ACCCACCCCG CTTTCGTAGT TTTCATTTAG AAAATAGAGA TTTTAAAAAT GTCCTGCCTT     658

TTAACGTAGA TATAAGCCTT CCCCCACTAC CGTAAATGTC CATTTATATC ATTTTTTATA     718

TATTCTTATA AAAATGTAAA AAAGAAAAAC ACCGCTTCTG CCTTTTCACT GTGTTGGAGT     778

TTTCTGGAGT GAGCACTCAC GCCCTAAGCG CACATTCATG TGGGCATTTC TTGCGAGCCT     838

CGCAGCCTCC GGAAGCTGTC GACTTCATGA CAAGCATTTT GTGAACTAGG GAAGCTCAGG     898

GGGGTTACTG GCTTCTCTTG AGTCACACTG CTAGCAAATG GCAGAACCAA AGCTCAAATA     958

AAAATAAAAT TATTTTCATT CATTCACTCA AAAAAA                               994

(2) INFORMATION FOR SEQ ID NO:2:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Pro Ala Ala Gly Ser Ser Met Glu Pro Ser Ala Asp Trp Leu
  1               5                  10                  15

Ala Thr Ala Ala Arg Gly Arg Val Glu Val Arg Ala Leu Leu
             20                  25                  30

Glu Ala Val Ala Leu Pro Asn Ala Pro Asn Ser Tyr Gly Arg Arg Pro
             35                  40                  45

Ile Gln Val Met Met Met Gly Ser Ala Arg Val Ala Glu Leu Leu Leu
 50                  55                  60

Leu His Gly Ala Glu Pro Asn Cys Ala Asp Pro Ala Thr Leu Thr Arg
 65                  70                  75                  80

Pro Val His Asp Ala Ala Arg Glu Gly Phe Leu Asp Thr Leu Val Val
             85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
            130                 135                 140

Ile Asp Ala Ala Glu Gly Pro Ser Asp Ile Pro Asp
145                 150                 155

(2) INFORMATION FOR SEQ ID NO:3:

(i) SEQUENCE CHARACTERISTICS:
        (A) LENGTH: 850 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 338..751
```

(xi) SEQUENCE DESCRIPTION: SEQ ID NO:3:

```
GCGGGGCAGT GAGGACTCCG CGACGGTCCG CACCCTGCGG CCAGAGCGGC TTTGAGCTCG      60

GCTGCTTCCG CGCTAGGCGC TTTTTCCCAG AAGCAATCCA GGCGCGCCCG CTGGTTCTTG     120

AGCGCCAGGA AAAGCCCGGA GCTAACGACC GGCCGCTCGG CACTGCACGG GGCCCCAAGC     180

CGCAGAAGAA GGACGACGGG AGGGTAATGA AGCTGAGCCC AGGTCTCCTA GGAAGGAGAG     240

AGTGCGCCGG AGCAGCGTGG GAAAGAAGGG AAGAGTGTCG TTAAGTTTAC GGCCAACGGT     300

GGATTATCCG GGCCGCTGCG CGTCTGGGGG CTGCGGA ATG CGC GAG GAG AAC AAG     355
                                          Met Arg Glu Glu Asn Lys
                                           1               5

GGC ATG CCC AGT GGG GGC GGC AGC GAT GAG GGT CTG GCC AGC GCC GCG     403
Gly Met Pro Ser Gly Gly Gly Ser Asp Glu Gly Leu Ala Ser Ala Ala
         10                  15                  20

GCG CGG GGA CTA GTG GAG AAG GTG CGA CAG CTC CTG GAA GCC GGC GCG     451
Ala Arg Gly Leu Val Glu Lys Val Arg Gln Leu Leu Glu Ala Gly Ala
         25                  30                  35

GAT CCC AAC GGA GTC AAC CGT TTC GGG AGG CGC GCG ATC CAG GTC ATG     499
Asp Pro Asn Gly Val Asn Arg Phe Gly Arg Arg Ala Ile Gln Val Met
     40                  45                  50

ATG ATG GGC AGC GCC CGC GTG GCG GAG CTG CTG CTG CTC CAC GGC GCG     547
Met Met Gly Ser Ala Arg Val Ala Glu Leu Leu Leu Leu His Gly Ala
 55                  60                  65                  70

GAG CCC AAC TGC GCA GAC CCT GCC ACT CTC ACC CGA CCG GTG CAT GAT     595
Glu Pro Asn Cys Ala Asp Pro Ala Thr Leu Thr Arg Pro Val His Asp
             75                  80                  85

GCT GCC CGG GAG GGC TTC CTG GAC ACG CTG GTG GTG CTG CAC CGG GCC     643
Ala Ala Arg Glu Gly Phe Leu Asp Thr Leu Val Val Leu His Arg Ala
             90                  95                 100

GGG GCG CGG CTG GAC GTG CGC GAT GCC TGG GGT CGT CTG CCC GTG GAC     691
Gly Ala Arg Leu Asp Val Arg Asp Ala Trp Gly Arg Leu Pro Val Asp
            105                 110                 115

TTG GCC GAG GAG CGG GGC CAC CGC GAC GTT GCA GGG TAC CTG CGC ACA     739
Leu Ala Glu Glu Arg Gly His Arg Asp Val Ala Gly Tyr Leu Arg Thr
            120                 125                 130

GCC ACG GGG GAC TGACGCCAGG TTCCCCAGCC GCCCACAACG ACTTTATTTT         791
Ala Thr Gly Asp
135

CTTACCCAAT TTCCCACCCC CACCCACCTA ATTCGATGAA GGCTGCCAAC GGGGAGCGG    850
```

(2) INFORMATION FOR SEQ ID NO:4:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:4:

```
Met Arg Glu Glu Asn Lys Gly Met Pro Ser Gly Gly Gly Ser Asp Glu
 1               5                  10                  15

Gly Leu Ala Ser Ala Ala Ala Arg Gly Leu Val Glu Lys Val Arg Gln
                 20                  25                  30

Leu Leu Glu Ala Gly Ala Asp Pro Asn Gly Val Asn Arg Phe Gly Arg
             35                  40                  45

Arg Ala Ile Gln Val Met Met Met Gly Ser Ala Arg Val Ala Glu Leu
         50                  55                  60

Leu Leu Leu His Gly Ala Glu Pro Asn Cys Ala Asp Pro Ala Thr Leu
 65                  70                  75                  80
```

```
Thr Arg Pro Val His Asp Ala Ala Arg Glu Gly Phe Leu Asp Thr Leu
                 85                  90                  95

Val Val Leu His Arg Ala Gly Ala Arg Leu Asp Val Arg Asp Ala Trp
            100                 105                 110

Gly Arg Leu Pro Val Asp Leu Ala Glu Glu Arg Gly His Arg Asp Val
        115                 120                 125

Ala Gly Tyr Leu Arg Thr Ala Thr Gly Asp
    130                 135
```

(2) INFORMATION FOR SEQ ID NO:5:

(i) SEQUENCE CHARACTERISTICS:
        (A) LENGTH: 857 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 82..582

(xi) SEQUENCE DESCRIPTION: SEQ ID NO:5:

```
ACTGGTCACA CGACTGGGCG ATTGGGCGGG CACTGAATCT CCGCGAGGAA AGCGAACTCG     60

AGGAGAGCCA TCTGGAGCAG C ATG GAG TCC GCT GCA GAC AGA CTG GCC AGG      111
                         Met Glu Ser Ala Ala Asp Arg Leu Ala Arg
                           1               5                  10

GCG GCC CAG GGC CGT GTG CAT GAC GTG CGG GCA CTG CTG GAA GCC GGG     159
Ala Ala Gln Gly Arg Val His Asp Val Arg Ala Leu Leu Glu Ala Gly
             15                  20                  25

GTT TCG CCC AAC GCC CCG AAC TCT TTC GGT CGT ACC CCG ATT CAG GTG     207
Val Ser Pro Asn Ala Pro Asn Ser Phe Gly Arg Thr Pro Ile Gln Val
         30                  35                  40

ATG ATG ATG GGC AAC GTT CAC GTA GCA GCT CTT CTG CTC AAC TAC GGT     255
Met Met Met Gly Asn Val His Val Ala Ala Leu Leu Leu Asn Tyr Gly
             45                  50                  55

GCA GAT TCG AAC TGC GAG GAC CCC ACT ACC TTC TCC CGC CCG GTG CAC     303
Ala Asp Ser Asn Cys Glu Asp Pro Thr Thr Phe Ser Arg Pro Val His
 60                  65                  70

GAC GCA GCG CGG GAA GGC TTC CTG GAC ACG CTG GTG GTG CTG CAC GGG     351
Asp Ala Ala Arg Glu Gly Phe Leu Asp Thr Leu Val Val Leu His Gly
 75                  80                  85                  90

TCA GGG GCT CGG CTG GAT GTG CGC GAT GCC TGG GGT CGC CTG CCG CTC     399
Ser Gly Ala Arg Leu Asp Val Arg Asp Ala Trp Gly Arg Leu Pro Leu
             95                 100                 105

GAC TTG GCC CAA GAG CGG GGA CAT CAA GAC ATC GTG CGA TAT TTG CGT     447
Asp Leu Ala Gln Glu Arg Gly His Gln Asp Ile Val Arg Tyr Leu Arg
        110                 115                 120

TCC GCT GGG TGC TCT TTG TGT TCC GCT GGG TGG TCT TTG TGT ACC GCT     495
Ser Ala Gly Cys Ser Leu Cys Ser Ala Gly Trp Ser Leu Cys Thr Ala
    125                 130                 135

GGG AAC GTC GCC CAG ACC GAC GGG CAT AGC TTC AGC TCA AGC ACG CCC     543
Gly Asn Val Ala Gln Thr Asp Gly His Ser Phe Ser Ser Ser Thr Pro
140                 145                 150

AGG GCC CTG GAA CTT CGC GGC CAA TCC CAA GAG CAG AGC TAAATCCGCC      592
Arg Ala Leu Glu Leu Arg Gly Gln Ser Gln Glu Gln Ser
155                 160                 165

TCAGCCCGCC TTTTTCTTCT TAGCTTCACT TCTAGCGATG CTAGCGTGTC TAGCATGTGG   652

CTTTAAAAAA TACATAATAA TGCTTTTTTT GCAATCACGG GAGGGAGCAG AGGGAGGGAG   712
```

```
CAGAAGGAGG GAGGGAGGGA GGGAGGGACT TCGACAGGAA AGGAATTGCA TGAGAAACTG      772

AGCGAAGGCG GCGGCGAAGG GAATAATGGC TGGATTGTTT AAAAAAATAA AATAAAGATA      832

CTTTTTAAAA TGTCAAAAAA AAAAA                                            857
```

(2) INFORMATION FOR SEQ ID NO:6:

(i) SEQUENCE CHARACTERISTICS:
        (A) LENGTH: 167 amino acids
        (B) TYPE: amino acid
        (D) TOPOLOGY: linear (ii) MOLECULE TYPE: protein (xi) SEQUENCE DESCRIPTION: SEQ ID NO:6:

```
Met Glu Ser Ala Ala Asp Arg Leu Ala Arg Ala Ala Gln Gly Arg Val
  1               5                  10                  15

His Asp Val Arg Ala Leu Leu Glu Ala Gly Val Ser Pro Asn Ala Pro
                 20                  25                  30

Asn Ser Phe Gly Arg Thr Pro Ile Gln Val Met Met Met Gly Asn Val
             35                  40                  45

His Val Ala Ala Leu Leu Leu Asn Tyr Gly Ala Asp Ser Asn Cys Glu
         50                  55                  60

Asp Pro Thr Thr Phe Ser Arg Pro Val His Asp Ala Ala Arg Glu Gly
 65                  70                  75                  80

Phe Leu Asp Thr Leu Val Val Leu His Gly Ser Gly Ala Arg Leu Asp
                 85                  90                  95

Val Arg Asp Ala Trp Gly Arg Leu Pro Leu Asp Leu Ala Gln Glu Arg
                100                 105                 110

Gly His Gln Asp Ile Val Arg Tyr Leu Arg Ser Ala Gly Cys Ser Leu
            115                 120                 125

Cys Ser Ala Gly Trp Ser Leu Cys Thr Ala Gly Asn Val Ala Gln Thr
        130                 135                 140

Asp Gly His Ser Phe Ser Ser Ser Thr Pro Arg Ala Leu Glu Leu Arg
145                 150                 155                 160

Gly Gln Ser Gln Glu Gln Ser
                165
```

(2) INFORMATION FOR SEQ ID NO:7:

(i) SEQUENCE CHARACTERISTICS:
        (A) LENGTH: 580 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 91..480

(xi) SEQUENCE DESCRIPTION: SEQ ID NO:7:

```
CTCCAGAGGG GAGGAGCCGC TCAGAGACCA GGCTGTAGCA ATCTCACGGC CGGCGAAGGA       60

CCATTTCTGC CACAGACCGG GGACAAGGGC ATG TTG GGC GGC AGC AGT GAC GCG      114
                                 Met Leu Gly Gly Ser Ser Asp Ala
                                   1               5

GGC CTG GCC ACC GCC GCG GCG CGG GGG CAA GTG GAG ACG GTG CGG CAG       162
Gly Leu Ala Thr Ala Ala Ala Arg Gly Gln Val Glu Thr Val Arg Gln
     10                  15                  20

CTC CTG GAA GCC GGC GCA GAT CCC AAC GCC CTG AAC CGC TTC GGG AGG       210
Leu Leu Glu Ala Gly Ala Asp Pro Asn Ala Leu Asn Arg Phe Gly Arg
```

```
            25                  30                  35                  40
CGC CCA ATC CAG GTC ATG ATG ATG GGC AGC GCC AGG GTG GCA GAG CTG         258
Arg Pro Ile Gln Val Met Met Met Gly Ser Ala Arg Val Ala Glu Leu
                    45                  50                  55

CTG CTG CTC CAC GGA GCA GAA CCC AAC TGC GCC GAC CCT GCC ACC CTT         306
Leu Leu Leu His Gly Ala Glu Pro Asn Cys Ala Asp Pro Ala Thr Leu
                60                  65                  70

ACC AGA CCT GTG CAC GAC GCA GCT CGG GAA GGC TTC CTG GAC ACG CTT         354
Thr Arg Pro Val His Asp Ala Ala Arg Glu Gly Phe Leu Asp Thr Leu
            75                  80                  85

GTC GTG CTG CAC CGG GCA GGG GCG CGG TTG GAT GTG TGT GAC GCC TGG         402
Val Val Leu His Arg Ala Gly Ala Arg Leu Asp Val Cys Asp Ala Trp
        90                  95                  100

GGC CGC CTG CCG GTA GAC TTG GCT GAA GAG CAG GGC CAC CGT GAC ATT         450
Gly Arg Leu Pro Val Asp Leu Ala Glu Glu Gln Gly His Arg Asp Ile
105                 110                 115                 120

GCG AGG TAT CTG CAC GCT GCC ACT GGA GAT TGACTGCGGG TTCCCTCCGC           500
Ala Arg Tyr Leu His Ala Ala Thr Gly Asp
                125                 130

CTTCCGCAAG GACTTCTTTC TCCCCAGCCC CATCTAGGAA GACTGTAAGC ACGAAGAGGC       560

CACCAGCGCC CAGCCTGCAG                                                   580

(2) INFORMATION FOR SEQ ID NO:8:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO:8:

Met Leu Gly Gly Ser Ser Asp Ala Gly Leu Ala Thr Ala Ala Arg
 1               5                  10                  15

Gly Gln Val Glu Thr Val Arg Gln Leu Leu Glu Ala Gly Ala Asp Pro
                20                  25                  30

Asn Ala Leu Asn Arg Phe Gly Arg Arg Pro Ile Gln Val Met Met Met
            35                  40                  45

Gly Ser Ala Arg Val Ala Glu Leu Leu Leu Leu His Gly Ala Glu Pro
        50                  55                  60

Asn Cys Ala Asp Pro Ala Thr Leu Thr Arg Pro Val His Asp Ala Ala
65                  70                  75                  80

Arg Glu Gly Phe Leu Asp Thr Leu Val Val Leu His Arg Ala Gly Ala
                85                  90                  95

Arg Leu Asp Val Cys Asp Ala Trp Gly Arg Leu Pro Val Asp Leu Ala
            100                 105                 110

Glu Glu Gln Gly His Arg Asp Ile Ala Arg Tyr Leu His Ala Ala Thr
        115                 120                 125

Gly Asp
130

(2) INFORMATION FOR SEQ ID NO:9:

(i) SEQUENCE CHARACTERISTICS:
        (A) LENGTH: 694 base pairs
        (B) TYPE: nucleic acid
        (C) STRANDEDNESS: both
        (D) TOPOLOGY: linear (ii) MOLECULE TYPE: cDNA
```

(ix) FEATURE:
    (A) NAME/KEY: CDS
    (B) LOCATION: 79..582

(xi) SEQUENCE DESCRIPTION: SEQ ID NO:9:

```
CCTCGAGATT TACCCTGCGA AGGACCTGAC TCTGAAATTC TGCCTCAAAT CACCACTGTG        60

AACAAGGGAC CCTAAAGA ATG GCC GAG CCT TGG GGG AAC GAG TTG GCG TCC        111
                   Met Ala Glu Pro Trp Gly Asn Glu Leu Ala Ser
                     1               5                      10

GCA GCT GCC AGG GGG GAC CTA GAG CAA CTT ACT AGT TTG TTG CAA AAT        159
Ala Ala Ala Arg Gly Asp Leu Glu Gln Leu Thr Ser Leu Leu Gln Asn
             15                  20                  25

AAT GTA AAC GTC AAC GCT CAA AAT GGA TTT GGG AGA ACT GCG CTG CAG        207
Asn Val Asn Val Asn Ala Gln Asn Gly Phe Gly Arg Thr Ala Leu Gln
         30                  35                  40

GTT ATG AAA CTT GGA AAT CCG GAG ATT GCC AGG AGG CTT CTC CTC AGA        255
Val Met Lys Leu Gly Asn Pro Glu Ile Ala Arg Arg Leu Leu Leu Arg
     45                  50                  55

GGT GCT AAT CCC AAT TTG AAA GAT GGA ACT GGT TTT GCT GTC ATT CAT        303
Gly Ala Asn Pro Asn Leu Lys Asp Gly Thr Gly Phe Ala Val Ile His
 60                  65                  70                  75

GAT GCT GCC AGA GCA GGT TTC CTG GAC ACT GTA CAG GCT TTG CTG GAG        351
Asp Ala Ala Arg Ala Gly Phe Leu Asp Thr Val Gln Ala Leu Leu Glu
                 80                  85                  90

TTC CAG GCT GAT GTT AAC ATT GAA GAT AAT GAA GGG AAC CTG CCC TTG        399
Phe Gln Ala Asp Val Asn Ile Glu Asp Asn Glu Gly Asn Leu Pro Leu
             95                 100                 105

CAC TTG GCT GCC AAA GAA GGC CAC CTC CCT GTG GTG GAG TTC CTT ATG        447
His Leu Ala Ala Lys Glu Gly His Leu Pro Val Val Glu Phe Leu Met
         110                 115                 120

AAG CAC ACA GCC TGC AAT GTG GGG CAT CGG AAC CAT AAG GGG GAC ACC        495
Lys His Thr Ala Cys Asn Val Gly His Arg Asn His Lys Gly Asp Thr
     125                 130                 135

GCC TTC GAC TTG GCC AGG TTC TAT GGA AGA AAT GAG GTC ATT AGC CTG        543
Ala Phe Asp Leu Ala Arg Phe Tyr Gly Arg Asn Glu Val Ile Ser Leu
140                 145                 150                 155

ATG GAG GCA AAT GGG GTT GGG GGA GCC ACA AGC CTG CAG TGAATGTGTA        592
Met Glu Ala Asn Gly Val Gly Gly Ala Thr Ser Leu Gln
                160                 165

GAGGTCTCTC TCACTGACCT CACACTGTCC GTTAGTTGGT TGGCTGTCCG TTTCACTATC       652

ACTTATTAAA ATATAGGGTT TCTTCGCTTT GTTTTAAAAT AT                          694
```

(2) INFORMATION FOR SEQ ID NO:10:

(i) SEQUENCE CHARACTERISTICS:
       (A) LENGTH: 168 amino acids
       (B) TYPE: amino acid
       (D) TOPOLOGY: linear (ii) MOLECULE TYPE: protein (xi) SEQUENCE DESCRIPTION: SEQ ID NO:10:

```
Met Ala Glu Pro Trp Gly Asn Glu Leu Ala Ser Ala Ala Ala Arg Gly
  1               5                  10                  15

Asp Leu Glu Gln Leu Thr Ser Leu Leu Gln Asn Asn Val Asn Val Asn
             20                  25                  30

Ala Gln Asn Gly Phe Gly Arg Thr Ala Leu Gln Val Met Lys Leu Gly
         35                  40                  45

Asn Pro Glu Ile Ala Arg Arg Leu Leu Leu Arg Gly Ala Asn Pro Asn
     50                  55                  60
```

```
Leu Lys Asp Gly Thr Gly Phe Ala Val Ile His Asp Ala Ala Arg Ala
 65                  70                  75                  80

Gly Phe Leu Asp Thr Val Gln Ala Leu Leu Glu Phe Gln Ala Asp Val
                 85                  90                  95

Asn Ile Glu Asp Asn Glu Gly Asn Leu Pro Leu His Leu Ala Ala Lys
            100                 105                 110

Glu Gly His Leu Pro Val Val Glu Phe Leu Met Lys His Thr Ala Cys
        115                 120                 125

Asn Val Gly His Arg Asn His Lys Gly Asp Thr Ala Phe Asp Leu Ala
    130                 135                 140

Arg Phe Tyr Gly Arg Asn Glu Val Ile Ser Leu Met Glu Ala Asn Gly
145                 150                 155                 160

Val Gly Gly Ala Thr Ser Leu Gln
                165
```

(2) INFORMATION FOR SEQ ID NO:11:

(i) SEQUENCE CHARACTERISTICS:
        (A) LENGTH: 941 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 134..631

(xi) SEQUENCE DESCRIPTION: SEQ ID NO:11:

```
CGAATTCGGC ACGAGAGTTG GCCCTGGTGG CACCGCAGTC CCTAGAGTTC TGATCCAGCT      60

CTTGCTGGTT CCCCAGCCCT GACCTTAACT GGGCTTGGGG CTGGGTGGGT TTCACAGTCC     120

ACCGGTATCC ACT ATG CTT CTG GAA GAA GTC TGC GTC GGC GAC CGG TTG       169
            Met Leu Leu Glu Glu Val Cys Val Gly Asp Arg Leu
              1               5                  10

AGT GGC GCA CGG GCC CGT GGC GAC GTG CAA GAG GTC CGC CGC CTT CTT       217
Ser Gly Ala Arg Ala Arg Gly Asp Val Gln Glu Val Arg Arg Leu Leu
         15                  20                  25

CAC CGG GAG CTG GTG CAT CCT GAC GCC CTG AAC CGC TTT GGC AAG ACG       265
His Arg Glu Leu Val His Pro Asp Ala Leu Asn Arg Phe Gly Lys Thr
 30                  35                  40

GCC TTG CAG GTC ATG ATG TTT GGA AGT CCA GCA GTT GCT TTG GAG CTC       313
Ala Leu Gln Val Met Met Phe Gly Ser Pro Ala Val Ala Leu Glu Leu
 45                  50                  55                  60

CTG AAG CAA GGT GCC AGC CCC AAT GTC CAA GAT GCC TCC GGT ACT AGT       361
Leu Lys Gln Gly Ala Ser Pro Asn Val Gln Asp Ala Ser Gly Thr Ser
                 65                  70                  75

CCT GTG CAT GAT GCG GCT CGC ACC GGG TTC CTG GAC ACC CTG AAG GTT       409
Pro Val His Asp Ala Ala Arg Thr Gly Phe Leu Asp Thr Leu Lys Val
             80                  85                  90

CTG GTG GAG CAT GGT GCT GAT GTC AAT GCC CTG GAC AGC ACT GGG TCG       457
Leu Val Glu His Gly Ala Asp Val Asn Ala Leu Asp Ser Thr Gly Ser
         95                 100                 105

CTC CCC ATC CAT CTG GCG ATA AGA GAG GGC CAT AGC TCC GTG GTC AGC       505
Leu Pro Ile His Leu Ala Ile Arg Glu Gly His Ser Ser Val Val Ser
110                 115                 120

TTC CTA GCT CCT GAA TCT GAT CTC CAC CAC AGG GAC GCT TCC GGT CTC       553
Phe Leu Ala Pro Glu Ser Asp Leu His His Arg Asp Ala Ser Gly Leu
125                 130                 135                 140

ACT CCC CTG GAG TTG GCT CGG CAG AGA GGG GCT CAG AAC CTC ATG GAC       601
Thr Pro Leu Glu Leu Ala Arg Gln Arg Gly Ala Gln Asn Leu Met Asp
```

```
                    145                 150                 155
ATT CTG CAG GGG CAC ATG ATG ATC CCA ATG TGACCCAAGG CCACTGTCTC          651
Ile Leu Gln Gly His Met Met Ile Pro Met
            160                 165

CAGCCTTACT GGGTTACTTG TCAACAAAAG AGGAAAGAAA CTTTCTCTTT TCACACCTGT      711

CCATTGAAGA AGGGAGTGGG AGGAGCAGTT TGTGGTTTAT TGGTGTTGAT TTCTTGAGTG      771

TGTGTGTTTG GGGGTGTTT CTCATTTGTT TTTCCTCACC CCTTTTGGTG TGTTGGAAAA       831

GAAGGGTCCT ACAGGCAACA GATCTAAATG GTTCAGTTTC CTCTGCACTG GGGCTGCACC      891

AGGGCAGGGG TTAAAGCCCT AGCCTCAGAG TGAGGTCATC ACTTCCCGGG                 941

(2) INFORMATION FOR SEQ ID NO:12:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:12:

Met Leu Leu Glu Glu Val Cys Val Gly Asp Arg Leu Ser Gly Ala Arg
 1               5                  10                  15

Ala Arg Gly Asp Val Gln Glu Val Arg Arg Leu Leu His Arg Glu Leu
            20                  25                  30

Val His Pro Asp Ala Leu Asn Arg Phe Gly Lys Thr Ala Leu Gln Val
        35                  40                  45

Met Met Phe Gly Ser Pro Ala Val Ala Leu Glu Leu Leu Lys Gln Gly
    50                  55                  60

Ala Ser Pro Asn Val Gln Asp Ala Ser Gly Thr Ser Pro Val His Asp
65                  70                  75                  80

Ala Ala Arg Thr Gly Phe Leu Asp Thr Leu Lys Val Leu Val Glu His
                85                  90                  95

Gly Ala Asp Val Asn Ala Leu Asp Ser Thr Gly Ser Leu Pro Ile His
            100                 105                 110

Leu Ala Ile Arg Glu Gly His Ser Ser Val Val Ser Phe Leu Ala Pro
        115                 120                 125

Glu Ser Asp Leu His His Arg Asp Ala Ser Gly Leu Thr Pro Leu Glu
    130                 135                 140

Leu Ala Arg Gln Arg Gly Ala Gln Asn Leu Met Asp Ile Leu Gln Gly
145                 150                 155                 160

His Met Met Ile Pro Met
            165

(2) INFORMATION FOR SEQ ID NO:13:

(i) SEQUENCE CHARACTERISTICS:
        (A) LENGTH: 912 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..909

(xi) SEQUENCE DESCRIPTION: SEQ ID NO:13:

ATG GCT GCC ACT CGA TAT GAA CCC GTG GCT GAA ATT GGT GTC GGT GCC       48
Met Ala Ala Thr Arg Tyr Glu Pro Val Ala Glu Ile Gly Val Gly Ala
```

```
  1               5                    10                    15
TAT GGG ACG GTG TAC AAA GCC CGA GAT CCC CAC AGT GGC CAC TTT GTG      96
Tyr Gly Thr Val Tyr Lys Ala Arg Asp Pro His Ser Gly His Phe Val
            20                  25                  30

GCC CTC AAG AGT GTG AGA GTT CCT AAT GGA GGA GCA GCT GGA GGG GGC     144
Ala Leu Lys Ser Val Arg Val Pro Asn Gly Gly Ala Ala Gly Gly Gly
        35                  40                  45

CTT CCC GTC AGC ACA GTT CGT GAG GTG GCC TTG TTA AGG AGG CTG GAG     192
Leu Pro Val Ser Thr Val Arg Glu Val Ala Leu Leu Arg Arg Leu Glu
    50                  55                  60

GCC TTT GAA CAT CCC AAT GTT GTA CGG CTG ATG GAT GTC TGT GCT ACT     240
Ala Phe Glu His Pro Asn Val Val Arg Leu Met Asp Val Cys Ala Thr
65                  70                  75                  80

TCC CGA ACT GAT CGG GAC ATC AAG GTC ACC CTA GTG TTT GAG CAT ATA     288
Ser Arg Thr Asp Arg Asp Ile Lys Val Thr Leu Val Phe Glu His Ile
                85                  90                  95

GAC CAG GAC CTG AGG ACA TAC CTG GAC AAA GCA CCT CCA CCG GGC CTG     336
Asp Gln Asp Leu Arg Thr Tyr Leu Asp Lys Ala Pro Pro Pro Gly Leu
            100                 105                 110

CCG GTT GAG ACC ATT AAG GAT CTA ATG CGT CAG TTT CTA AGC GGC CTG     384
Pro Val Glu Thr Ile Lys Asp Leu Met Arg Gln Phe Leu Ser Gly Leu
        115                 120                 125

GAT TTT CTT CAT GCA AAC TGC ATT GTT CAC CGG GAC CTG AAG CCA GAG     432
Asp Phe Leu His Ala Asn Cys Ile Val His Arg Asp Leu Lys Pro Glu
130                 135                 140

AAC ATT CTA GTG ACA AGT AAT GGG ACC GTC AAG CTG GCT GAC TTT GGC     480
Asn Ile Leu Val Thr Ser Asn Gly Thr Val Lys Leu Ala Asp Phe Gly
145                 150                 155                 160

CTA GCT AGA ATC TAC AGC TAC CAG ATG GCC CTC ACG CCT GTG GTG GTT     528
Leu Ala Arg Ile Tyr Ser Tyr Gln Met Ala Leu Thr Pro Val Val Val
                165                 170                 175

ACG CTC TGG TAC CGA GCT CCT GAA GTT CTT CTG CAG TCT ACA TAC GCA     576
Thr Leu Trp Tyr Arg Ala Pro Glu Val Leu Leu Gln Ser Thr Tyr Ala
            180                 185                 190

ACA CCC GTG GAC ATG TGG AGC GTT GGC TGT ATC TTT GCA GAG ATG TTC     624
Thr Pro Val Asp Met Trp Ser Val Gly Cys Ile Phe Ala Glu Met Phe
        195                 200                 205

CGT CGG AAG CCT CTC TTC TGT GGA AAC TCT GAA GCC GAC CAG TTG GGG     672
Arg Arg Lys Pro Leu Phe Cys Gly Asn Ser Glu Ala Asp Gln Leu Gly
    210                 215                 220

AAA ATC TTT GAT CTC ATT GGA TTG CCT CCA GAA GAC GAC TGG CCT CGA     720
Lys Ile Phe Asp Leu Ile Gly Leu Pro Pro Glu Asp Asp Trp Pro Arg
225                 230                 235                 240

GAG GTA TCT CTA CCT CGA GGA GCC TTT GCC CCC AGA GGG CCT CGG CCA     768
Glu Val Ser Leu Pro Arg Gly Ala Phe Ala Pro Arg Gly Pro Arg Pro
                245                 250                 255

GTG CAG TCA GTG GTG CCA GAG ATG GAG GAG TCT GGA GCG CAG CTG CTA     816
Val Gln Ser Val Val Pro Glu Met Glu Glu Ser Gly Ala Gln Leu Leu
            260                 265                 270

CTG GAA ATG CTG ACC TTT AAC CCA CAT AAG CGA ATC TCT GCC TTC CGA     864
Leu Glu Met Leu Thr Phe Asn Pro His Lys Arg Ile Ser Ala Phe Arg
        275                 280                 285

GCC CTG CAG CAC TCC TAC CTG CAC AAG GAG GAA AGC GAC GCA GAG         909
Ala Leu Gln His Ser Tyr Leu His Lys Glu Glu Ser Asp Ala Glu
    290                 295                 300

TGA                                                                 912
```